(12) United States Patent  
Mograbi et al.

(10) Patent No.: US 9,474,763 B2  
(45) Date of Patent: Oct. 25, 2016

(54) COMPOSITIONS AND METHODS FOR AMELIORATION AND PREVENTION OF DRUG-INDUCED TOXICITY

(71) Applicants: Hadasit Medical Research Services and Development Ltd., Jerusalem (IL); Josef Mograbi, Tel Aviv (IL)

(72) Inventors: Josef Mograbi, Tel Aviv (IL); Yaron Ilan, Jerusalem (IL)

(73) Assignee: Hadasit Medical Research Services and Development Ltd., Jerusalem (IL)

(*) Notice: Subject to any disclaimer, the term of this patent is extended or adjusted under 35 U.S.C. 154(b) by 0 days.

(21) Appl. No.: 14/551,724

(22) Filed: Nov. 24, 2014

(65) Prior Publication Data

US 2015/0080348 A1    Mar. 19, 2015

Related U.S. Application Data

(63) Continuation of application No. PCT/IL2013/050446, filed on May 23, 2013.

(60) Provisional application No. 61/654,971, filed on Jun. 4, 2012, provisional application No. 61/651,005, filed on May 24, 2012.

(51) Int. Cl.

| | |
|---|---|
| *A61K 31/357* | (2006.01) |
| *C07D 309/36* | (2006.01) |
| *A61K 31/661* | (2006.01) |
| *A61K 45/06* | (2006.01) |
| *A61K 31/10* | (2006.01) |
| *A61K 31/167* | (2006.01) |
| *A61K 31/198* | (2006.01) |
| *A61K 31/685* | (2006.01) |
| *A61K 31/7056* | (2006.01) |
| *A61K 31/7076* | (2006.01) |
| *A61K 31/197* | (2006.01) |

(52) U.S. Cl.  
CPC ............ *A61K 31/661* (2013.01); *A61K 31/10* (2013.01); *A61K 31/167* (2013.01); *A61K 31/197* (2013.01); *A61K 31/198* (2013.01); *A61K 31/357* (2013.01); *A61K 31/685* (2013.01); *A61K 31/7056* (2013.01); *A61K 31/7076* (2013.01); *A61K 45/06* (2013.01)

(58) Field of Classification Search  
CPC ........................... A61K 31/357; C07D 309/36  
See application file for complete search history.

(56) References Cited

U.S. PATENT DOCUMENTS

| | | | |
|---|---|---|---|
| 4,868,114 A | 9/1989 | Nagasawa et al. | |
| 6,495,170 B1 | 12/2002 | Smit et al. | |
| 6,555,141 B1 | 4/2003 | Corson et al. | |
| 6,566,401 B2 | 5/2003 | Herzenberg et al. | |
| 6,576,267 B2 | 6/2003 | Gelber et al. | |
| 6,863,906 B2 | 3/2005 | Henderson et al. | |
| 7,238,373 B2 | 7/2007 | Meyrowitz | |
| 7,563,779 B2 | 7/2009 | Henderson et al. | |
| 7,723,389 B2 | 5/2010 | Herzenberg et al. | |
| 8,148,356 B2 | 4/2012 | Pavliv | |
| 2001/0000472 A1* | 4/2001 | Henderson | A61K 36/28 424/725 |
| 2007/0021376 A1 | 1/2007 | Giampapa | |
| 2011/0124718 A1* | 5/2011 | McCain | A61K 36/28 514/452 |
| 2012/0022161 A1 | 1/2012 | Pavliv | |

FOREIGN PATENT DOCUMENTS

| | | |
|---|---|---|
| WO | 2005/094862 A1 | 10/2005 |
| WO | 2009097874 A1 | 8/2009 |
| WO | 2011044230 A2 | 4/2011 |

OTHER PUBLICATIONS

Lee, D., et al. "Molecular Structure and Stereochemistry of Silybin A, Silybin B, Isosilybin A, and Isosilybin B, Isolated from *Silybum marianum* (Milk Thistle)." J. Nat. Prod. (2003), vol. 66, pp. 1171-1174).*

WebMD. "Acetaminophen Liver Damage Directory." © Nov. 19, 2011. Available from: < http://www.webmd.com/pain-management/acetaminophen-liver-damage-directory >.*

RxList.com. "Percocet." © Jan. 14, 2012. Available from: < http://web.archive.org/web/20120114190338/http://www.rxlist.com/percocet-drug/warnings-precautions.htm >.*

McNeil-PPC. "Tylenol® Sinus Congestion & Pain Caplets (Daytime)." © 2011. Available from: < http://www.tylenol.com/products/tylenol-sinus-congestion-pain-caplets-daytime >.*

McNeil-PPC. "Tylenol® Cough and Sore Throat." © 2010. Available from: < http://dailymed.nlm.nih.gov/dailymed/archives/fdaDrugInfo.cfm?archiveid=43326 >.*

Drugs.com. "Acetaminophen/Diphenhydramine Dosage." (c) Feb. 2012. Available from: < http://web.archive.org/web/20120215211820/http://www.drugs.com/dosage/acetaminophen-diphenhydramine.html >.*

Drugs.com. "Acetaminophen and guaifenesin." © Feb. 2009. Available from: < http://web.archive.org/web/20090201110251/http://www.drugs.com/mtm/acetaminophen-and-guaifenesin.html >.*

(Continued)

*Primary Examiner* — Andrew D Kosar  
*Assistant Examiner* — John S Kenyon  
(74) *Attorney, Agent, or Firm* — Vorys, Sater, Seymour and Pease LLP

(57) ABSTRACT

Pharmaceutical compositions including combinations of protective agents selected from isosilybin B, methylsulfonylmethane (MSM), phosphatidylcholine, cysteine (Cys), seleno-cysteine (Se-Cys), ribose-cysteine (RibCys), N-acetylcysteine (NAC), N-acetylcysteine-amide (AD4), methionine (Met) and S-adenosylmethionine (SAM) for reducing and/or preventing drug-induced toxicity, such as acetaminophen-induced toxicity. The compositions may be formulated with or without acetaminophen, and accordingly may be used as safe formulations of acetaminophen with reduced risk of causing liver damage, or as an antidote for the treatment of acetaminophen overdose. Methods for treating acetaminophen intoxication.

8 Claims, 5 Drawing Sheets

(56) References Cited

OTHER PUBLICATIONS

Bessems and Vermeulen (2001) Paracetamol (acetaminophen)-induced toxicity: molecular and biochemical mechanisms, analogues and protective approaches. Crit Rev Toxicol 31(1): 55-138.

Blakely and McDonald (1995) Acute renal failure due to acetaminophen ingestion: a case report and review of the literature. J Am Soc Nephrol 6(1): 48-53.

Bower et al., (2007) Population-based surveillance for acute liver failure. Am J Gastroenterol 102(11): 2459-63.

Bray et al., (1992) S-adenosylmethionine protects against acetaminophen hepatotoxicity in two mouse models. Hepatology 15(2): 297-301.

Chassaing et al., (1999) Determination of reduced and oxidized homocysteine and related thiols in plasma by thiol-specific pre-column derivatization and capillary electrophoresis with laser-induced fluorescence detection. J Chromatogr B Biomed Sci Appl 735(2): 219-27.

Chun et al., (2009) Acetaminophen hepatotoxicity and acute liver failure. J Clin Gastroenterol 43(4): 342-9.

Darbar et al., (2011) Antihepatoprotective potential of Livina, a polyherbal preparation on parcetamol induced hepatotoxicity: a comparison with Silymarin. Asian Journal of Pharmaceutical and Clinical Research 4(1): 72-77.

Dvorák et al., (2003) Primary cultures of human hepatocytes as a tool in cytotoxicity studies: cell protection against model toxins by flavonolignans obtained from Silybum marianum. Toxicol Lett 137(3): 201-12.

Kaufman et al., (2002) Recent patterns of medication use in the ambulatory adult population of the United States: the Slone survey. JAMA 287(3): 337-44.

Khashab et al., (2007) Epidemiology of acute liver failure. Curr Gastroenterol Rep 9(1): 66-73.

Lai et al., (2006) 2005 Annual Report of the American Association of Poison Control Centers' national poisoning and exposure database. Clin Toxicol (Phila) 44(6-7): 803-932.

Larson et al., (2005) Acetaminophen-induced acute liver failure: results of a United States multicenter, prospective study. Hepatology 42(6): 1364-72.

Lee (2003) Acute liver failure in the United States. Semin Liver Dis 23(3): 217-26.

Murray et al., (2008) Drug-related hepatotoxicity and acute liver failure. J Pediatr Gastroenterol Nutr 47(4): 395-405.

Nourjah et al., (2006) Estimates of acetaminophen (Paracetomal)-associated overdoses in the United States. Pharmacoepidemiol Drug Saf 15(6): 398-405.

O'Riordan et al., (2011) Acute kidney injury in patients admitted to a liver intensive therapy unit with paracetamol-induced hepatotoxicity. Nephrol Dial Transplant 26(11): 3501-8.

Ostapowicz et al., (2002) Results of a prospective study of acute liver failure at 17 tertiary care centers in the United States. Ann Intern Med 137(12): 947-54.

Polyaket al., (2010) Identification of hepatoprotective flavonolignans from silymarin. Proc Natl Acad Sci U S A 107(13): 5995-9.

Rakela et al., (1985) Fulminant hepatitis: Mayo Clinic experience with 34 cases. Mayo Clin Proc 60(5): 289-92.

Slitt et al., (2005) Effect of ribose cysteine pretreatment on hepatic and renal acetaminophen metabolite formation and glutathione depletion. Basic Clin Pharmacol Toxicol 96(6): 487-94.

Stern et al., (2005) Contribution of acetaminophen-cysteine to acetaminophen nephrotoxicity II. Possible involvement of the gamma-glutamyl cycle. Toxicol Appl Pharmacol 202(2): 160-71.

Stern et al., (2005) Contribution of acetaminophen-cysteine to acetaminophen nephrotoxicity in CD-1 mice: I. Enhancement of acetaminophen nephrotoxicity by acetaminophen-cysteine. Toxicol Appl Pharmacol 202(2): 151-9.

FDA, "Acetaminophen Overdose and Liver Injury—Background and Options for Reducing Injury"; dated May 22, 2009. Retrieved from the internet on Mar. 14, 2012.

Legalon SIL Mushroom Poisoning Clinical Study. URL: https://sites.google.com/site/legalonsil/; retrieved on Dec. 28, 2011.

Wiley—Blackwell. "Milk thistle herb protects cancer patients from chemotherapy-associated liver toxicity." ScienceDaily. ScienceDaily, Dec. 27, 2009. www.sciencedaily.com/releases/2009/12/091215172325.htm.

Jaeschke et al., (2003) The role of oxidant stress and reactive nitrogen species in acetaminophen hepatotoxicity. Toxicol Lett 144(3): 279-288.

Nakhostin-Roohi et al., (2011) Effect of chronic supplementation with methylsulfonylmethane on oxidative stress following acute exercise in untrained healthy men. J Pharm Pharmacol 63(10): 1290-1294.

Woodhead et al., "An analysis of N-acetylcysteine treatment for acetaminophen overdose using a systems model of drug-induced liver injury", J Pharmacol Exp Ther, vol. 342, No. 2, pp. 529-540, (2012).

* cited by examiner 4 mg APAP        4 mg APAP+        4 mg APAP+
                 3.5 mg NAC        3.5 mg NAC,
                                   3h later: 0.9 mg of PC 4 mg APAP        4 mg APAP+        4 mg APAP+
                 3.5 mg NAC        3.5 mg NAC,
                                   1.5 mg MSM

| 4.6 mg APAP | APAP – 4.6 mg<br>NAC – 3.5 mg | APAP – 4.6 mg<br>Cys – 3.5 mg | APAP – 4.6 mg<br>Met – 3.5 mg |

COMPOSITIONS AND METHODS FOR AMELIORATION AND PREVENTION OF DRUG-INDUCED TOXICITY

FIELD OF THE INVENTION

The present invention relates to the treatment and prevention of drug-induced toxicity, such as liver and kidney toxicity. In particular, the present invention relates to compositions and methods useful in treating, reducing and/or preventing liver failure, liver injury, liver damage and other toxicity effects associated with acetaminophen or caused by acetaminophen overdose.

BACKGROUND OF THE INVENTION

Acetaminophen (chemically named N-(4-hydroxyphenyl) acetamide), also known as para-acetylaminophenol, paracetamol and N-acetyl-para-aminophenol (abbreviated as APAP), is a widely used analgesic and antipyretic drug. It is commonly used for the relief of headaches and other minor pains, and is a major ingredient in various cold and flu remedies.

Acetaminophen is the generic name of a drug found in many common brand-name over-the-counter (OTC) and prescription (Rx) products. In some products acetaminophen is the sole active ingredient (e.g., TYLENOL®), while in others it is combined with additional active ingredients, such as opioid analgesics, nasal decongestants, cough suppressants and antihistamines. Examples include combinations with oxycodone (e.g. PERCOCET®) and hydrocodone (e.g. VICODIN®). Acetaminophen is available as a tablet, capsule, liquid suspension, suppository, intravenous, and intramuscular form.

While generally safe for use at recommended doses (up to 1,000 mg per single dose and up to 4,000 mg per day for adults), acute overdoses of acetaminophen can cause serious liver injury, acute liver failure (ALF) and even death. In effect, acetaminophen-induced liver toxicity is the most prevalent cause of acute liver failure in the Western world. In addition, several drug-host interactions, such as drug viral interactions were suggested as potential causes for acetaminophen-induced liver toxicity even without exceeding the recommended dosages.

In the liver, acetaminophen is metabolized through several pathways before being eliminated from the body. One of these pathways, which involves the cytochrome P-450 systems, yields a toxic intermediate known as N-acetyl-p-benzo-quinone imine (NAPQI). Normally, this toxic metabolite is detoxified by conjugation to reduced glutathione. However, an excessive amount of acetaminophen in the liver, and accordingly excessive amounts of NAPQI, results in shortage of reduced glutathione and accumulation of the toxic metabolite. The toxic metabolite then binds to liver proteins and cause cellular injury. The amount of the accumulated toxic metabolite and the difficulty of the liver to eliminate it before it causes damage influence the extent of liver injury. NAPQI accumulation is only one of the suggested explanations for acetaminophen-induced liver toxicity.

In addition, the immune system was suggested to play a major role in the pathogenesis of the toxic effect and the liver injury. Both NK and NKT cells as well as several cytokines were suggested as important factors in this context.

Despite a number of efforts since the early 1990s to reduce the incidence of acetaminophen-related liver injury, the extent of liver failure cases reported in the medical literature indicates that liver injury from acetaminophen overdose remains a serious public health problem.

In addition to the liver, renal damage is also associated with acetaminophen consumption. In toxic amounts, acetaminophen may result in acute tubular necrosis. At therapeutic dosages, acetaminophen can be toxic in patients with risk factors such as starvation and chronic ingestion of alcohol or certain medications. Long term consumption of normal doses of acetaminophen has also been found to result in cumulative damage to the kidneys.

Many cases of acetaminophen overdose are caused unintentionally by consumers inadvertently taking more than the recommended dose. A number of factors that may contribute to acetaminophen overdose problem have been identified, including: the narrow safety margin of acetaminophen, risk factors rendering some individuals specially and specifically prone to acetaminophen-induced liver injury, such as excessive alcohol consumption and pre-existing liver disorders, insufficient public knowledge about the serious risks of acetaminophen overdose, and the availability of many different types of OTC and Rx products containing acetaminophen and possibly other active ingredients, and a variety of doses for different indications. The latter may result in the consumption of more than one acetaminophen containing product without realizing that acetaminophen is included in all of these products, and accordingly an increased risk of acetaminophen overdose. In addition, it can be difficult to recognize and diagnose the onset of liver injury.

Current treatments of acetaminophen overdose are mainly aimed at removing acetaminophen from the body and trying to replace diminished glutathione levels. Oral administration of activated charcoal can also be used to decrease absorption of acetaminophen by binding any drug remaining in the gastrointestinal tract. The treatment also includes administration of an antidote, N-acetylcysteine (NAC), which is a known precursor for glutathione, thereby helping the body to regenerate reduced glutathione and prevent or reduce damage to the liver. A liver transplant is sometimes required if damage to the liver becomes severe and irreversible.

The known treatments have several drawbacks, mainly due to their limited therapeutic window. Actions such as gastric lavage or administration of activated charcoal are effective only in cases where the patients present for treatment soon after taking the overdose. NAC is considered effective only when administered within 8 hours following intoxication, after which the efficacy is significantly reduced.

Patients with acute overdose, or with liver toxicity due to any dose, can deteriorate into fulminant liver failure. Although some of these patients will recover spontaneously, for some of them, liver transplantation is the only way to prevent deterioration and death.

There are currently no commercially available formulations of acetaminophen which purposely intended to reduce the risk of liver toxicity.

U.S. Pat. No. 4,868,114 discloses a method comprising stimulating the biosynthesis of glutathione in mammalian cells by contacting the cells with an effective amount of cysteine prodrugs.

U.S. Pat. No. 6,555,141 discloses therapeutic compositions for the protection, treatment and repair of liver tissue comprising two or more compounds selected from the group consisting of S-adenosylmethionine, L-ergothioneine, and a compound selected from the group consisting of Milk thistle (*Silybum marianum*), silymarin and active components of silymarin, whether naturally, synthetically, or semi-synthetically derived, and to methods of preventing and treating liver disease and of repairing damaged liver tissue.

U.S. Pat. No. 6,566,401 discloses pharmaceutical compositions for the treatment or prevention of the toxic effects of therapeutic agents and methods of treating or preventing such toxicity using a toxicity reducing amount of N-acetylcysteine either alone or in combination with a therapeutically effective amount or, to achieve its therapeutic advantages, an amount larger than what is customarily given as a therapeutically effective amount, of a therapeutic agent.

U.S. Pat. No. 7,238,373 discloses a nutritional supplement that is designed to provide nutritional benefits as well as to assist the body with detoxification.

U.S. Pat. No. 8,148,356 discloses acetylcysteine compositions in solution, comprising acetylcysteine and which are substantially free of metal chelating agents, such as EDTA. Further, this invention relates to methods of making and using the acetylcysteine compositions. The present compositions and methods are designed to improve patient tolerance and compliance, while at the same time maintaining the stability of the pharmaceutical formulation. The compositions and methods of this invention are useful in the treatment of acetaminophen overdose, acute liver failure, various cancers, methacrylonitrile poisoning, reperfusion injury during cardio bypass surgery, and radiocontrast-induced nephropathy, and can also be used as a mucolytic agent.

US 2011/0124718 discloses the reduction of acetaminophen toxicity by dietary milk thistle extract. Milk thistle and acetaminophen are combined to provide single dosages containing both ingredients, whether dispensed in a liquid suspension, chewable tablets, coated caplets, gelcaps, geltabs, and suppositories.

US 2012/0022161 discloses a pharmaceutical composition and method for providing a reduction in side effects for human patients in need of therapy comprising the administration of a pharmaceutical composition comprising acetylcysteine.

WO 2009/097874 discloses compositions comprising a combination of amino acids selected from: a) L-Cysteine with L-Methionine; b) L-Cysteine with L-Serine; c) L-Cysteine with L-Methionine and L-Serine; d) L-Methionine with L-Serine; or precursors or transporters of said amino acids, for the prevention of paracetamol-induced liver damage.

WO 2011/044230 discloses methods and compositions comprising N-acetylcysteine amide (NAC amide) and derivatives thereof for use in treatments and prophylactic therapies for human and non-human mammalian diseases, disorders, conditions and pathologies associated with bomb blast or other high energy noise or impulse blasts. Pharmaceutically or physiologically acceptable compositions of NAC amide or derivatives thereof are also provided, which may be administered alone, or in combination with other suitable agents.

Polyak et al. (2010) *PNAS U.S.A*, 107; (5995-5999), report the identification of hepatoprotective flavonolignans from silymarin.

There still remains an unmet need for more effective compositions and methods for treating or preventing drug toxicity, e.g. liver damage caused by acetaminophen. There is a further need for novel compositions of acetaminophen characterized by decreased risk of inducing toxicity while preserving efficacy. Such compositions may be useful for reducing or even preventing acetaminophen-related toxicity.

SUMMARY OF THE INVENTION

The present invention provides pharmaceutical compositions comprising combinations of protective agents which are effective in reducing and/or preventing drug-induced toxicity, including but not limited to, acetaminophen-induced toxicity. The protective agents utilized herein are selected from isosilybin B, methylsulfonylmethane (MSM), phosphatidylcholine, cysteine (Cys), seleno-cysteine (Se-Cys), ribose-cysteine (RibCys), N-acetylcysteine (NAC), N-acetylcysteine-amide (AD4), methionine (Met) and S-adenosylmethionine (SAM).

The pharmaceutical compositions containing the protective agents may be formulated with or without a drug or substance with potential toxicity, and accordingly may be used as safe formulations of the drug, or as an antidote in case of intoxication.

According to certain embodiments, the compositions are formulated with or without acetaminophen. Acetaminophen-containing compositions may be used as safe formulations with reduced risk of causing liver damage and/or renal damage. Compositions without acetaminophen can be used as an antidote for the treatment of acetaminophen-related toxicity, such as liver failure or liver disorder.

The present invention further provides methods for treating drug-induced intoxication, such as acetaminophen-induced intoxication, utilizing the combinations of protective agents disclosed herein.

The combinations of protective agents of the present invention were found to be remarkably effective in reducing liver damage and liver toxicity associated with acetaminophen administration. As exemplified herein below, mice exposed to sub-lethal amounts of acetaminophen administered with different combinations of the above compounds showed significantly reduced serum levels of liver enzymes and better body weight recovery following fast compared to mice exposed to same amounts of acetaminophen alone. In addition, histological examination revealed little or no liver damage in mice that received the different combinations of protective compounds, in contrast to mice who received acetaminophen alone. The ability of the compounds to protect the liver was demonstrated when the compounds and acetaminophen were administered concurrently, as well as when the compounds were administered several hours following acetaminophen administration. The combinations of the present invention act at least additively and preferably synergistically and are superior to the currently used antidote (gold standard treatment) of acetaminophen poisoning, namely, NAC alone.

According to one aspect, the present invention provides a pharmaceutical composition comprising isolated isosilybin B, and optionally further comprising at least one additional protective agent selected from the group consisting of methylsulfonylmethane (MSM), phosphatidylcholine, cysteine (Cys), seleno-cysteine (Se-Cys), ribose-cysteine (RibCys), N-acetylcysteine (NAC), N-acetylcysteine-amide (AD4), methionine (Met) and S-adenosylmethionine (SAM), wherein said pharmaceutical composition is effective in treating or preventing drug-induced toxicity.

As will be explained in more detail below, isosilybin B is one of the components of an extract produced from milk thistle (*Silybum marianum*). This compound is utilized herein in an isolated form, meaning that it is substantially separated from other components of the extract.

In some embodiments of the present invention, the composition comprises isolated isosilybin B and further comprises (i) one or more protective agents selected from the group consisting of Cys, Se-Cys, RibCys, NAC, AD4, Met and SAM; and (ii) one or more protective agents selected from the group consisting of MSM and phosphatidylcholine.

In some embodiments of the present invention, the pharmaceutical composition further comprises a pharmaceutically acceptable diluent, excipient or carrier.

In some embodiments of the present invention, the phosphatidylcholine component comprises a majority of unsaturated fatty acids. In some embodiments, the phosphatidylcholine component comprises a majority of polyunsaturated fatty acids. In some embodiments, the polyunsaturated phosphatidylcholine comprises unsaturated fatty acids selected from the group consisting of linoleic acid, linolenic acid and oleic acid. In some embodiments, linoleic acid constitutes about 70% or more of the fatty acid content of the phosphatidylcholine.

In some embodiments of the present invention, the phosphatidylcholine component comprises 1,2-dilinoleoylphosphatidylcholine (DLPC), with linoleic acid bound both in c1- and c2-positions of the molecule. In some embodiments, about 50% or more of the phosphatidylcholine molecules present within the composition are DLPC.

In some embodiments of the present invention, the pharmaceutical composition is used for the treatment of acetaminophen intoxication.

In some embodiments of the present invention, the protective agents described herein are formulated together with a drug that can potentially cause toxic effects, in a single pharmaceutical composition. Thus, in some embodiments, the pharmaceutical composition of the present invention further comprises a drug with potential toxicity. In some embodiments, the drug is acetaminophen. According to these embodiments, the pharmaceutical composition is characterized by a reduced risk of acetaminophen-induced toxicity, such as acetaminophen-induced liver damage and/or nephrotoxicity, compared to formulations of acetaminophen that do not contain the protective agents as described herein. Such compositions are contemplated to substantially retain the efficacy of the drug, e.g. acetaminophen, while significantly reducing or preventing drug-induced liver toxicity, liver damage and kidney damage.

In additional embodiments, the acetaminophen-containing pharmaceutical composition of the present invention further comprises at least one additional drug selected from the group consisting of an opioid analgesic, a decongestant, a cough suppressant, an antihistamine and an expectorant.

In some embodiments of the present invention, the opioid analgesic is selected from the group consisting of codeine, oxycodone, hydrocodone and propoxyphene.

In some embodiments, the decongestant is selected from the group consisting of phenylephrine and pseudoephedrine.

In some embodiments of the present invention, the expectorant is guaiphenesin.

In some embodiments of the present invention, the cough suppressant is selected from the group consisting of dextromethorphan and codeine.

In some embodiments of the present invention, the antihistamine is selected from the group consisting of chlorpheniramine, phenyltoloxamine and doxylamine.

Typically, the pharmaceutical composition is formulated for systemic administration. In some embodiments, the pharmaceutical composition is formulated for a route of administration selected from the group consisting of oral, rectal, intravenous, intramuscular, intradermal, subcutaneous and intranasal.

According to another aspect, the present invention provides a method for treating drug intoxication in a subject in need thereof, the method comprising administering to the subject isolated isosilybin B, and optionally at least one additional protective agent selected from the group consisting of MSM, phosphatidylcholine, Cys) Se-Cys, RibCys, NAC, AD4, Met and SAM.

In some embodiments of the present invention, the method comprises administering to the subject isolated isosilybin B and further administering (i) one or more protective agents selected from the group consisting of Cys, Se-Cys, RibCys, NAC, AD4, Met and SAM; and (ii) one or more protective agents selected from the group consisting of MSM and phosphatidylcholine.

When two or more protective agents are used to treat the drug intoxication, in some embodiments of the present invention, the protective agents are within a single composition. In other embodiments of the present invention, the protective agents are within separate compositions. In some embodiments, the two or more protective agents are administered concurrently. In other embodiments, the two or more protective agents are administered sequentially. In some embodiments, the two or more protective agents are administered via the same route of administration. In other embodiments, the two or more protective agents are administered via different routes of administration.

In some embodiments of the present invention, administration is performed via a route of administration selected from the group consisting of oral, rectal, intravenous, intramuscular, intradermal, subcutaneous and intranasal. In some embodiments, the route of administration is selected from the group consisting of oral and intravenous.

In some embodiments, the method of the present invention is applied to a subject who has consumed, or suspected of having consumed, large amounts of acetaminophen. In some embodiment, acetaminophen intoxication is acute intoxication. In other embodiments, acetaminophen intoxication is chronic intoxication.

In some embodiments of the present invention, the subject is human. In other embodiments, the subject is a non-human mammal.

According to another aspect, the present invention provides a composition comprising isolated isosilybin B, and optionally at least one additional protective agent selected from the group consisting of MSM, phosphatidylcholine, Cys, Se-Cys, RibCys, NAC, AD4, Met and SAM, for use in the treatment of drug intoxication.

In some embodiments, the drug is acetaminophen.

In some embodiments of the present invention, the pharmaceutical composition further comprises a pharmaceutically acceptable diluent, excipient or carrier.

In some embodiments of the present invention, the pharmaceutical composition is formulated for administration via a route of administration selected from the group consisting of oral, rectal, intravenous and intramuscular.

These and further aspects and features of the present invention will become apparent from the detailed description, examples and claims which follow.

DETAILED DESCRIPTION OF THE INVENTION

Figure 1:
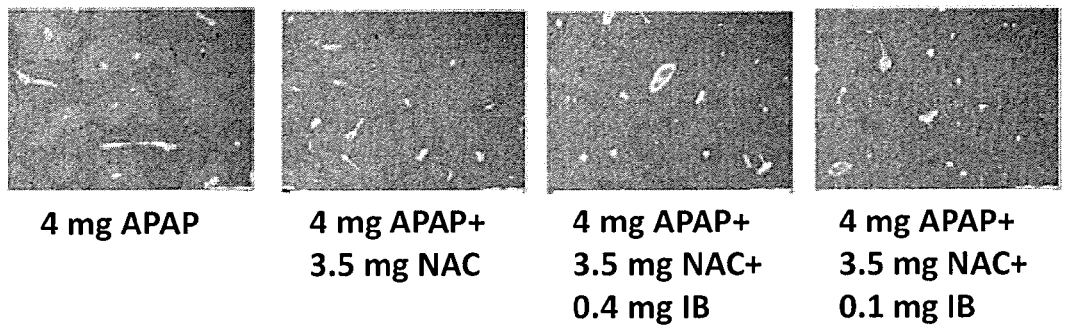
FIG. 1. Representative liver biopsy results of mice treated with acetaminophen in combination with NAC alone or NAC plus IB, compared to mice administered with acetaminophen only.

The present invention relates to treatment and prevention of drug-induced toxicity, particularly acetaminophen-induced toxicity, using protective active ingredients selected from the group consisting of isosilybin B, methylsulfonylmethane (MSM), phosphatidylcholine, cysteine (Cys), seleno-cysteine (Se-Cys), ribose-cysteine (RibCys), N-acetylcysteine (NAC), N-acetylcysteine-amide (AD4), methionine (Met) and S-adenosylmethionine (SAM). Typically, a plurality of protective active compounds is used.

As used herein, "a plurality" indicates at least two.

As used herein, a "protective agent" or "protective compound" refers to a compound effective in treating or preventing drug-induced toxicity. In particular, the term refers to a compound that serves to decrease hepatotoxicity and/or nephrotoxicity caused by the consumption of a drug. The term "drug" is used herein to refer to a compound with a therapeutic activity, most often a manmade small organic molecule, that can potentially cause toxic effects, such as damage to the liver and possible other organs, for example, acetaminophen. For the purposes of the application and claims, a drug is a molecule known to exhibit potential hepatotoxicity.

As used herein, the phrase "pharmaceutical composition effective in treating or preventing drug-induced toxicity", indicates that the protective agents are present in the pharmaceutical composition in an amount that is effective to perform their utility. When a drug is included in the composition, the phrase indicates that the protective agents are present in the composition in an amount that is effective to significantly reduce or even completely inhibit toxic effects of the drug. When a drug is not included in the composition, the phrase indicates that the amount of protective agents is effective in alleviating or even eliminating liver injury and/or other damage caused by the consumption of a drug.

As used herein "drug-induced toxicity" refers to damages to body tissues and organs resulting from the consumption of a drug, typically consumption of large amounts of the drug.

As used herein, the term "potential toxicity", when referring to a drug, indicates that the drug is generally safe when consumed at the recommended doses, but can be toxic when large amounts are consumed, and/or when consumed by a subject who is more susceptible to toxic effects of the drug.

As used herein, "drug intoxication" refers to a clinical condition resulting from the consumption of toxic amounts of a drug (e.g. acetaminophen) that damage the liver and/or other organs such as the kidneys.

As used herein, the terms "treating" and "treatment", when referring to drug-induced toxicity or drug intoxication, encompass reducing or even eliminating the drug-induced (for example, acetaminophen-induced) liver damage, and/or renal damage. The terms may also encompass improvement of other symptoms associated with intoxication, as detailed hereinbelow. The extent of liver damage, as well as improvement and reduction in liver damage as a result of utilizing the compositions and methods of the present invention, may be evaluated, for example, by measuring serum levels of liver enzymes. An increased level of liver enzymes in the serum indicates liver damage. Nephrotoxicity can be monitored, for example, through simple blood and urine tests. A decreased glomerular filtration rate (GFR) indicates renal damage and poor renal function.

As used herein, the term "preventing", when referring to drug-induced toxicity, encompasses significantly reducing the risk of toxicity or even completely inhibiting toxic effects of the drug.

As used herein, the term "about", when referring to a measurable value such as an amount, is meant to encompass variations of +/−10%, more preferably +/−5%, even more preferably +/−1%, and still more preferably +/−0.1% from the specified value, as such variations are appropriate to achieve the intended purpose.

Pharmaceutical Compositions

Pharmaceutical compositions of the present invention comprise protective agents selected from isosilybin B, MSM, phosphatidylcholine, Cys, Se-Cys, RibCys, NAC, AD4, Met and SAM. Pharmaceutically acceptable salts of the protective agents described herein are also within the scope of the present invention. The compositions may be formulated with or without a drug with potential toxicity, such as acetaminophen.

According to an aspect of the present invention, there is provided herein a pharmaceutical composition effective in treating or preventing drug-induced, such as acetaminophen-induced, liver toxicity, the composition comprising isolated isosilybin B, and optionally further comprising at least one more protective agent selected from the group consisting of MSM, phosphatidylcholine, Cys, Se-Cys, RibCys, NAC, AD4, Met and SAM. Each combination represents a separate embodiment of the invention.

According to another aspect of the present invention, there is provided herein a pharmaceutical composition comprising the combinations of protective agents disclosed herein, for use in the treatment of drug intoxication. In particular embodiments, the drug is acetaminophen.

In some embodiments, the pharmaceutical composition comprises isosilybin B. In some embodiments, isosilybin B is combined with at least one more protective agent selected from the group consisting of NAC, phosphatidylcholine, MSM, RibCys, AD4, Cys, Se-Cys, Met and SAM.

In some embodiments, the pharmaceutical composition comprises isolated isosilybin B and further comprises (i) one or more protective agents selected from the group consisting of Cys, Se-Cys, RibCys, NAC, AD4, Met and SAM; and (ii) one or more protective agents selected from the group consisting of MSM and phosphatidylcholine.

In some embodiments, the pharmaceutical composition comprises isolated isosilybin B, NAC and one or more protective agents selected from the group consisting of MSM and phosphatidylcholine.

In other embodiments, the pharmaceutical composition comprises isolated isosilybin B and further comprises (i) one or more protective agents selected from the group consisting of Cys, Se-Cys, RibCys, AD4, Met and SAM; and (ii) one or more protective agents selected from the group consisting of MSM and phosphatidylcholine.

In some embodiments, the pharmaceutical composition comprises isolated isosilybin B and further comprises (i) one or more protective agents selected from the group consisting of Cys and Met; and (ii) one or more protective agents selected from the group consisting of MSM and phosphatidylcholine.

In some embodiments, a pharmaceutical composition effective in treating or preventing drug-induced toxicity is provided, the composition comprises a plurality of protective agents selected from the group consisting of isolated isosilybin B, MSM, phosphatidylcholine, Cys, Se-Cys, RibCys, NAC, AD4, Met and SAM. Each combination represents a separate embodiment of the invention.

In some embodiments, the composition comprises NAC and at least one more protective agent selected from the group consisting of phosphatidylcholine, MSM, isosilybin B. In some embodiments, the combination of NAC and at least one more protective agent selected from the above compounds permits lower amounts of NAC in order to achieve a therapeutic effect compared to the amount required for NAC alone.

In some embodiments, the composition comprises (i) one or more protective agents selected from the group consisting of AD4, Cys, Se-Cys, RibCys, Met and SAM; and (ii) one or more protective agents selected from the group consisting of phosphatidylcholine, MSM, isosilybin B.

In some embodiments, the composition comprises a combination of two or more protective agents selected from the group consisting of NAC, phosphatidylcholine, MSM, isosilybin B, RibCys and SAM.

In some embodiments, the pharmaceutical composition comprises NAC and phosphatidylcholine as the protective agents. In additional embodiments, the pharmaceutical composition comprises NAC in combination with MSM or SAM as the protective agents. In yet additional embodiments, the pharmaceutical composition comprises NAC and isosilybin B as the protective agents. In some embodiments, the combination of NAC and at least one more protective agent selected from the above compounds permits lower amounts of NAC in order to achieve a therapeutic effect compared to the amount required for NAC alone.

In some embodiments, the pharmaceutical composition does not include NAC.

In some embodiments of the present invention, the compositions contain the protective agents described herein, and do not contain a drug that can cause intoxication. Such compositions are effective in treating drug-induced toxicity, and can be administered in case that drug-induced toxicity has occurred, in order to treat said toxicity. For example, such compositions can be administered following an overdose of a drug, which results in signs of intoxication, in order to treat the toxicity effects. In particular embodiments, the pharmaceutical compositions of the present invention can be used as an antidote for the treatment of acetaminophen intoxication.

In other embodiments, the compositions of the present invention contain the protective agents described herein, and further contain a drug that can cause intoxication. Such compositions are characterized by a reduced risk of drug intoxication compared to compositions that contain the drug without the protective agents.

In particular embodiments, the compositions contain acetaminophen and possibly additional one or more drugs. According to these embodiments, safe formulations of acetaminophen are provided, with significantly reduced risk of causing liver and renal damage, even when taken at large amounts. Such compositions have several advantages, including a significantly reduced risk for overdose and significantly reduced need for liver transplantation following an overdose. In addition, such compositions may be beneficial to populations at risk.

In some embodiments, a pharmaceutical composition is provided, which comprises acetaminophen, isosilybin B and at least one more protective agent selected from the group consisting of MSM, phosphatidylcholine, Cys, Se-Cys, RibCys, NAC, AD4, Met and SAM, said pharmaceutical composition is characterized by a reduced risk of drug intoxication compared to a pharmaceutical composition comprising acetaminophen without isosilybin B and the at least one more protective agent.

In some embodiments, a pharmaceutical composition is provided, which comprises acetaminophen and further comprises a plurality of protective agents selected from the group consisting of isolated isosilybin B, MSM, phosphatidylcholine, Cys, Se-Cys, RibCys, NAC, AD4, Met and SAM, said pharmaceutical composition is characterized by a reduced risk of drug intoxication compared to a pharmaceutical composition comprising acetaminophen without the plurality of protective agents.

The protective agents utilized herein are commercially available and may also be synthesized or extracted by methods known in the art or by new methods. NAC may be identified by CAS Registry Number 616-91-1, MSM may be identified by CAS Registry Number 67-71-0, isosilybin B may be identified by CAS Registry Number 142796-22-3, SAM may be identified by CAS Registry Number 29908-03-0, RibCys may be identified by CAS Registry Number 17087-36-4, AD4 may be identified by CAS Registry Number 38520-57-9, Cys may be identified by CAS Registry Number 52-90-4, Se-Cys may be identified by CAS Registry Number 10236-58-5, Met may be identified by CAS Registry Number 63-68-3.

Phosphatidylcholine is a phospholipid composed of a choline headgroup and glycerophosphoric acid with a variety of fatty acids. The fatty acids may include saturated and unsaturated fatty acids.

In some embodiments of the present invention, the phosphatidylcholine component comprises mostly unsaturated fatty acids. In some embodiments, the fatty acid content of the phosphatidylcholine comprises at least one of linoleic acid, linolenic acid and oleic acid. In some embodiments, linoleic acid constitutes about 70% or more of the fatty acid content of the phosphatidylcholine.

In some embodiments of the present invention, the phosphatidylcholine component comprises 1,2-dilinoleoylphosphatidylcholine (DLPC), with two linoleic acid molecules. In some embodiments, about 50% or more of the phosphatidylcholine molecules present within the composition are DLPC.

Isosilybin B (also known as isosilibinin B) is a flavonolignan that constitutes one of the components of the milk thistle (*Silybum marianum*) extract. Traditional milk thistle extract is made from the plant seeds and consists of about 65-80% silymarin (a flavonolignan complex) and 20-35% fatty acids. Silymarin is a complex mixture of polyphenolic molecules, including seven closely related flavonolignans, namely silybin A, silybin B, isosilybin A, isosilybin B, silychristin, isosilychristin and silydianin, and one flavonoid (taxifolin).

It is now disclosed that isosilybin B is highly more potent and effective in reducing acetaminophen-induced liver toxicity, compared to other compounds found in silymarin, or in any other milk thistle extract of any part of the plant. As exemplified herein below, the closely related silybin B and isosilybin A did not show a beneficial effect when administered to mice together with, or following, large dosage of acetaminophen. Isosilybin B may be purified from an extract of the milk thistle. Isosilybin B is utilized herein in an isolated form, that is separated from the other ingredients of the extract. As used herein, "isolated" indicates at least about 80%, separated from other ingredients of the extract, preferably at least about 90%, more preferably at least about 95% separated from other ingredients of the extract. Synthetic Isosilybin B may also be used.

In some embodiments, the NAC is substantially free of its oxidized form, di-n-acetylcysteine. It is preferred that the therapeutic agent, serially or co-administered, be in any form in which it is typically available and the composition should be prepared in a manner that substantially prevents oxidation of the NAC during preparation or storage.

In some embodiments of the invention, the preparation and storage of the formulation is performed in such a way that the reduced form of NAC is the primary form administered to the patient. Maintaining NAC containing formulations in solid form is preferable for this purpose. When in solution, NAC containing formulations are preferably stored in a dark bottle that is vacuum sealed. Storage in cool dark environments is also preferred.

The determination of reduced and oxidized species present in a sample may be determined by various methods known in the art, for example with capillary electrophoresis, HPLC, etc. as described by Chassaing et al. (1999) J Chromatogr B Biomed Sci Appl 735(2):219-27.

The protective agents described herein are present in the composition in an amount which is effective for inducing the therapeutic effect.

Identification of therapeutically effective amounts can be performed by methods well known to those skilled in the art. Exemplary dosage ranges for the different active protective agents (for human use, oral administration) include doses ranging between about 0.05-10 mg/kg, for example between about 0.05-5 mg/kg, between about 0.05-1 mg/kg, between about 0.1-2.5 mg/kg, between about 0.5-2 mg/kg.

In some embodiments, when two or more protective agents are present in the composition, they can be formulated such that they are released concurrently. In other embodiments, they are formulated such that they are released sequentially. For example, in case there are two protective agents within a pharmaceutical composition, one can be formulated for immediate release, and the other for sustained release. Such formulations are known in the art.

In some embodiments, the protective agents are formulated within liposomes. The liposomes may be used as a delivery method. The liposomes may be used for liver targeting. One or more of the protective agents may be used to create the liposomes.

In some embodiments, the pharmaceutical composition is a combination medication that further comprises acetaminophen. The composition may also include additional one or more drugs, such as opioid analgesics, decongestants, cough suppressants, antihistamines, expectorants or combinations thereof. Information about combination medications containing acetaminophen and at least one more active ingredient can be found, for example, at the MedLinePlus website.

Non-limiting examples of opioid analgesics include codeine, oxycodone, hydrocodone and propoxyphene. Non-limiting examples of decongestants include phenylephrine, pseudoephedrine and guaiphenesin. Non-limiting examples of cough suppressants include dextromethorphan and codeine. Non-limiting examples of antihistamines include chlorpheniramine, phenyltoloxamine and doxylamine. A non-limiting example of an expectorant is guaiphenesin.

Advantageously, the combination of the protective compounds described herein with acetaminophen (and optionally other drugs) does not interfere with the normal pharmaceutical activity of acetaminophen, and it maintains its pain relieving and fever reducing properties.

Acetaminophen is commercially available and may also be synthesized by methods well known in the art. An overview of synthetic processes of acetaminophen can be found, for example, in Anthony S. Travis (2007). "Manufacture and uses of the anilines: A vast array of processes and products". In Zvi Rappoport. The chemistry of Anilines Part 1. Wiley. p. 764; and Elmar Friderichs, Thomas Christoph, Helmut Buschmann (2005), "Analgesics and Antipyretics", Ullmann's Encyclopedia of Industrial Chemistry, Weinheim: Wiley-VCH The compositions of the present invention that comprise acetaminophen may find use as anti-pyretic and analgesic agents, and are suitable for medical indications treatable with acetaminophen alone. An improvement in product safety is provided by the inclusion of the protective compounds as disclosed herein, which substantially prevents the possibility of accidental or inadvertent overdose.

The amount of compounds in the compositions of the present invention which will be effective in the treatment of a particular condition will depend on the nature of the condition, and can be determined by standard clinical techniques. See, for example, Goodman and Gilman; The Physician's Desk Reference, Medical Economics Company, Inc., Oradell, N.J., 1995; and to Drug Facts and Comparisons, Facts and Comparisons, Inc., St. Louis, Mo., 1993.

As the addition of the compounds as disclosed herein does not affect the therapeutic efficacy of acetaminophen, it is generally not necessary to adjust the dosage from what would ordinarily be administered for acetaminophen alone, and in fact the dose may be raised due to the increased safety of the present formulations. The precise dose to be employed in the formulation will also depend on the route of administration, and the seriousness of the disease, and should be decided according to the judgment of the practitioner and each patient's circumstances.

For example, the acetaminophen present in orally administrable solid unit doses will usually be at least about 80 mg (for pediatric doses), 325 mg, 500 mg and 650 mg. Oral liquid dosage forms usually comprise at least about 100 mg/ml, 120 mg/2.5 ml, 120 mg/5 ml, 160 mg/5 ml, 165 mg/5 ml, 325 mg/5 ml acetaminophen.

Suppositories are formulated in the manner well known in the art and usually comprise at least about 120 mg, 125 mg, 325 mg, 500 mg and 650 mg acetaminophen per dosage unit Typically, the composition further comprises a pharmaceutically acceptable diluent, excipient or carrier.

As used herein, the term "pharmaceutically acceptable diluent, excipient, or carrier" refers to a diluent, excipient, or carrier that does not cause significant irritation to an organism and does not abrogate the biological activity and properties of the administered active agent.

As used herein, the term "excipient" refers to an inert substance added to a pharmaceutical composition to further facilitate administration of an active ingredient. Non-limiting examples of excipients include calcium carbonate, calcium phosphate, various sugars and types of starch, cellulose derivatives, gelatin, vegetable oils, and polyethylene glycols. Techniques for formulation and administration of drugs may be found in "Remington's Pharmaceutical Sciences", Mack Publishing Co., Easton, Pa., (Remington: The Science and Practice of Pharmacy, Gennaro, A., Lippincott, Williams & Wilkins, Philadelphia, Pa., 20th ed, 2000).

As used herein, a "carrier" refers to any substance suitable as a vehicle for delivering of the agents or molecule of the present invention to a suitable in vivo or in vitro site. As such, carriers can act as a pharmaceutically acceptable excipient of a therapeutic composition of the present invention. Carriers of the present invention include: (1) excipients or formularies that transport, but do not specifically target a molecule to a cell (referred to herein as non-targeting carriers); and (2) excipients or formularies that deliver a molecule to a specific site in a subject or a specific cell (i.e., targeting carriers). Examples of non-targeting carriers include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Therapeutic compositions of the present invention can be sterilized by conventional methods.

Any suitable route of administration may be used for the composition of the present invention, including but not limited to local and systemic routes. Systemic administration includes all enteral and all parenteral routes. Non-limiting examples of suitable administration routes include oral, rectal, transmucosal such as transnasal and buccal, intravenous, intramuscular, transdermal, subcutaneous, intradermal, intravitreal, intravesicular and inhalation routes.

Thus, in some embodiments, the composition of the present invention is formulated for topical administration. In other embodiments, the composition is formulated for systemic administration.

Pharmaceutical compositions of the present invention may be formulated in conventional manners. The proper formulation is dependent upon the route of administration chosen.

In some embodiments, the compositions of the present invention are formulated for oral administration. Non-limiting examples of formulations for oral administration include tablets, pills, dragees, capsules, liquids, gels, syrups, slurries, suspensions, and the like, for oral ingestion by a patient. Suitable carriers for oral administration are well known in the art. Compositions for oral use can be made using a solid excipient, optionally grinding the resulting mixture, and processing the mixture of granules, after adding suitable auxiliaries as desired, to obtain tablets or dragee cores. Non-limiting examples of suitable excipients include fillers such as sugars, including lactose, sucrose, mannitol, or sorbitol, cellulose preparations such as, maize starch, wheat starch, rice starch, potato starch, gelatin, gum tragacanth, methyl cellulose, hydroxypropylmethyl-cellulose, and sodium carbomethylcellulose, and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

For administration by injection, the active ingredients of the composition may be formulated in aqueous solutions, for example in physiologically compatible buffers including but not limited to Hank's solution, Ringer's solution, or physiological salt buffer. Formulations for injection may be presented in unit dosage forms, for example, in ampoules, or in multi-dose containers with, optionally, an added preservative. The compositions may be in the form of suspensions, solutions, or emulsions in oily or aqueous vehicles, and may contain formulatory agents such as suspending, stabilizing, and/or dispersing agents. Non-limiting examples of suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions. Alternatively, the active ingredient may be in powder form for constitution with a suitable vehicle, for example, a sterile, pyrogen-free, water-based solution, before use. For intravenous administration, it is preferable to adjust the pH of the administered solution to that of the blood, namely, about pH=7.4.

For transmucosal administration, penetrants appropriate to the barrier to be permeated are used in the formulation. Such penetrants are generally known in the art.

For buccal administration, the compositions may take the form of tablets or lozenges formulated in conventional manner.

For administration by inhalation route, the active ingredients are conveniently delivered in the form of an aerosol spray presentation from a pressurized pack or a nebulizer with the use of a suitable propellant, for example, dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

In some embodiments, the compositions of the present invention are formulated for rectal administration, for example, as suppositories or retention enemas, using, for example, conventional suppository bases such as cocoa butter or other glycerides.

The exact formulation, route of administration, and dosage can be chosen by the individual physician in view of the patient's condition.

In some embodiments, the composition further comprises at least one additive useful in the pharmaceutical fields, including, but not limited to fats, emulsifiers and co-emulsifiers, hydrophilic or lipophilic gelling agents, colorants, fragrances, emollients, humectants, preservatives, vitamins, chelators, solvents, fillers, thickeners, hydrophilic and lipophilic filters, dyestuffs, neutralizers, penetration-enhancing agents and polymers.

Non-limiting examples of suitable fats include mineral oils, oils of animal origin (lanolin), synthetic oils (isopropyl myristate, octyldodecyl, isostearyl isostearate, decyl oleate or isopropyl palmitate), silicone oils (cyclomethicone or dimethicone) and fluorinated oils. Fatty alcohol, fatty acids, waxes and gums, notably silicone gums and elastomers can also be used as fats.

Non-limiting examples of suitable emulsifiers and co-emulsifiers include polyglycerol fatty acid esters, sucrose fatty acid esters, sorbitane fatty acid esters, oxyethylene sorbitan fatty acid esters, PEG fatty alcohol ethers, glycerol fatty acid esters, alkyl sulphates, alkyl ether sulphates, alkyl phosphates, alkyl polyglucosides and dimethicone copolyols.

Non-limiting examples of suitable hydrophilic gelling include carboxyvinyl polymers (carbomer), acrylic copolymers such as acrylate/alkylacrylate copolymers, polyacrylamids, polysaccharides such as xanthan gum, guar gum, natural gums such as cellulose gum and derivatives, clays and 2-acrylamido-2-methylpropane acid copolymers.

Non-limiting examples of suitable lipophilic gelling agents include modified clays such as bentones, fatty acid metal salts, hydrophobic silica and ethylcellulose.

Non-limiting examples of suitable fillers include talc, kaolin, mica, serecite, magnesium carbonate, aluminum silicate and organic powders such as nylon.

Non-limiting examples of suitable dyestuffs include lipophilic dyes, hydrophilic dyes, pigments and mother-of-pearl commonly used in cosmetic or dermatological compositions, and their mixtures.

Non-limiting examples of suitable neutralizers include soda, triethanolamine, aminomethyl propanol and potassium hydroxide.

Non-limiting examples of suitable penetration enhancing agents include alcohols and glycols (ethanol and propylene glycol), ethoxydiglycol, alcohols and fatty acids (oleic acid), fatty acid esters and dimethyl isosorbide.

Non-limiting examples of preservatives compatible with cosmetic and pharmaceutical compositions include benzoic acid, its salts and esters, sorbic acid and its salts, parabens and their salts, triclosan, imidazolidinyl urea, phenoxyethanol, DMDM hydantoin, diazolidinyl urea and chlorphenesin.

Conventionally, the filters are UVA and UVB filters. Non-limiting examples of suitable UVA and UVB filters include organic filters such as benzophenone-3, butyl methoxydibenzoyl methane, octocrylene, octyl methoxycinnamate, 4-methylbenzylidene camphor, octyl salicylate, terephthalylidene dicamphor sulfonic acid and drometrizole trisiloxane, and non-organic filters such as titanium oxide and zinc oxide.

Non-limiting examples of suitable solvents include water, ethanol, glycerin, propylene glycol, butylene glycol and sorbitol.

The quantities of these various additives are those conventionally used in pharmaceutical preparations as is known to a person skilled in the art.

Methods and Uses

According to an aspect of the present invention, there is provided herein a method for treating acetaminophen intoxication in a subject in need thereof, the method comprising administering the combinations of protective agents disclosed herein. In some embodiments, isolated isosilybin B, alone or in combination with one or more one more protective agents selected from the group consisting of MSM, phosphatidylcholine, Cys) Se-Cys, RibCys, NAC, AD4, Met and SAM are administered. In some embodiments, two or more protective agents are administered, selected from the group consisting of NAC, AD4, Cys, Se-Cys, Met, RibCys phosphatidylcholine, MSM, and isosilybin B.

The administered protective agents may be present in the same of different compositions. The administered protective agents may be administered concurrently or sequentially. The administered protective agents may be administered via the same or different routes of administration.

The compositions and methods of the present invention are typically employed for the treatment of a mammal, preferably a human.

The acetaminophen intoxication includes both acute and chronic intoxication.

According to some conventions, acute intoxication may be defined as consuming total ≥150 mg/kg (about 7.5 g in adults) within 24 h. This equals 24 regular-strength tablets over 8 hours or less. However any other dose, including even one pill, may induce toxicity.

Chronic intoxication may occur as a result of long period of low dose consumption, excessive use or repeated overdose.

The symptoms of intoxication may include abdominal pain, appetite loss, coma, convulsions, diarrhea, irritability, jaundice, nausea, sweating, pallor, upset stomach and/or vomiting. Symptoms may also include elevations in the plasma levels of hepatic enzymes and bilirubin, prolongation of the prothrombin time, hypoglycemia and/or lactic acidosis.

Information about acute and chronic acetaminophen intoxication can be found, for example, in The Merck Manual.

In some embodiments, administration of the compositions as disclosed herein provides a prolonged therapeutic window compared with the conventional, commercially available treatment, meaning that they are effective for a longer period of time following overdose or intoxication. In some embodiments, the therapeutic efficacy is maintained up to 10 hours or more, up to 10-15 hours, up to 15-24 hours, up to 24 hours or more, up to 48 hours or more.

The present invention further provides the use of the protective agents described herein, for the manufacture of a medicament for the treatment of drug intoxication. In some embodiments, the drug is acetaminophen.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Mice: Male C57BL/6, 9-10 or 11-12 weeks old

Reagents:

Phosphatidylcholine (PC)—PhosChol®, Nutrasal (Nutrasal.Com, Westbrook, Me. 04092, made in USA), liquid, kept in room temperature (R/T). Concentration: 3000 mg PC per 5 ml=600 mg/ml. The solution was diluted to 60 mg/ml (stock solution).

N-acetyl-para-aminophenol (APAP)—Tiptipot®, CTS group (made in Israel), liquid.

N-acetylcysteine (NAC)—Flumil™ 2 gr, antidote 20% (Pharmazam), 10 ml.

Isosilybin B (IB)—Sigma, Israel, Cat. No. 59527. 5 mg was emulsified in 1000 μl of DDW (di-distilled water) to yield a 5 mg/ml solution which was kept in 4° C.

Methylsulfonylmethane (MSM)—99.9% pure LIGNISUL MSM—CRYSTAL HEALTH, powder (made in USA) was dissolved in phosphate buffer saline (PBS).

L-Cysteine (Cys): Sigma, Israel (powder, 25 gr) dissolved with DDW to 25 mg/ml, PH=5.16.

L-Methionine (Met): Sigma, Israel (powder, 25 gr) dissolved with DDW to 50 mg/ml. PH=5.84

Example 1

Isosilybin B (IB)

IB was tested for its effect on toxicity induced by APAP in comparison to NAC using the following procedure: Mice were allocated into four groups of six mice each, as described in Table 1 below. The mice received sub-lethal hepatotoxic doses of APAP, causing liver damage equivalent to consumption of approximately 10 gr APAP (20 caplets of 500 mg) per 70 kg man.

TABLE 1

Groups and treatment regimens

| Group | N | Treatment | Dosage (for treatment) | Admin. | fasting |
|---|---|---|---|---|---|
| A | 6 | APAP | 4 mg/mouse | PO | yes |
| B | 6 | APAP + NAC | APAP - 4 mg/mouse NAC - 3 mg/mouse | PO | yes |
| C | 6 | APAP + IB | APAP - 4 mg/mouse IB - 0.4 mg/mouse | PO | yes |
| D | 6 | APAP + IB | APAP - 4 mg/mouse IB - 0.2 mg/mouse | PO | yes |
| E | 6 | APAP + IB | APAP - 4 mg/mouse IB - 0.1 mg/mouse | PO | yes |

Mice were treated according to the following procedure:
Food was taken on the afternoon (18:00) of Day 0. Mice were orally administered APAP, APAP+IB or APAP+NAC 15 h hours later (9:00 next morning, Day 1) by gavage administration. A total of 350 μl were administered, containing the different components in the desired concentrations in PBS. Food was returned 2 h after APAP administration (Day 1). For all groups, mice were weighted daily, and blood samples were taken 24 h hours after APAP administration (Day 2). Serum levels of the liver enzymes aspartate aminotransferase (AST) and alanine aminotransferase (ALT) were measured using a Reflovet® Plus clinical chemistry analyzer (Roche Diagnostics, GmbH, Mannheim, Germany). Serum samples were diluted before the measurements, as needed.

Table 2 presents the effect of each compound on the serum levels of the liver enzymes ALT and AST.

TABLE 2

Serum levels of liver enzymes (IU/L)

| Group | ALT (average ± std. dev.) | AST (average ± std. dev.) |
|---|---|---|
| 4 mg APAP | 14,360 ± 4,370.52 | 18,920.00 ± 12,192.04 |
| 4 mg APAP + 3 mg NAC | 513.63 ± 644.37 | 781.33 ± 402.23 |
| 4 mg APAP + 0.4 mg IB | 8,656.67 ± 4,212.24 | 4,856.00 ± 2,751.61 |
| 4 mg APAP + 0.2 mg IB | 9,050 ± 3,703.18 | 4,746.67 ± 2,130.45 |
| 4 mg APAP + 0.1 mg IB | 7,717.60 ± 7,388.76 | 5,047.60 ± 5,533.58 |

As can be seen from the above table, IB showed a protective effect when administered with APAP, leading to lower ALT/AST serum levels compared to administration of APAP alone (about 40% and 75% reduction, respectively, compared to administration of APAP only (p<0.05). Advantageously, this effect was observed for relatively low doses of IB, ranging from 0.1-0.4 mg/mouse.

In addition, mice that received APAP with IB showed lower body weight loss between Day 0 and Day 2, compared to mice that received APAP only (p<0.01).

Example 2

Comparative

The following combinations were tested using the same procedure described in Example 1 above, and compared to 4 mg APAP+3 or 3.5 mg NAC:
4 mg APAP+0.1 mg Isosilybin A (IA)
4 mg APAP+0.2 mg IA
4 mg APAP+0.4 mg IA
4 mg APAP+0.1 mg silybin B
4 mg APAP+0.4 mg silybin B
The results are summarized in Tables 3 and 4.

TABLE 3

Serum levels of liver enzymes (IU/L)

| Group | ALT (average ± std. dev.) | AST (average ± std. dev.) |
|---|---|---|
| 4 mg APAP | 5,617.50 ± 1,832.77 | 3,672.67 ± 1,965.99 |
| 4 mg APAP + 3 mg NAC | 1,050.25 ± 1,248.13 | 2,717.33 ± 3,314.47 |
| 4 mg APAP + 0.4 mg IA | 7,010.00 ± 1,952.85 | 4,720.67 ± 1,909.82 |
| 4 mg APAP + 0.2 mg IA | 6,976.75 ± 4,473.26 | 5,349.33 ± 3,537.58 |
| 4 mg APAP + 0.1 mg IA | 8,002.50 ± 2,122.65 | 5,468.00 ± 1,986.15 |

TABLE 4

Serum levels of liver enzymes (IU/L)

| Group | ALT (average ± std. dev.) | AST (average ± std. dev.) |
|---|---|---|
| 4 mg APAP | 8,880.00 ± 2,624.31 | 5,848.67 ± 1,993.43 |
| 4 mg APAP + 3.5 mg NAC | 807.00 ± 706.48 | 816.40 ± 501.92 |
| 4 mg APAP + 0.4 mg silybin B | 7,217.50 ± 3,466.48 | 4,610.00 ± 2,764.22 |
| 4 mg APAP + 0.1 mg silybin B | 11,240.00 ± 5,088.05 | 5,836.67 ± 3,256.90 |

As can be seen from the above tables, administration of additional ingredients from the milk thistle extract, namely, Isosilybin A and silybin B was shown to be ineffective in reducing liver enzymes serum levels.

Example 3

IB in Combination with NAC

A combination of IB and NAC was tested for its effect on toxicity induced by APAP using the same procedure described in Example 1 above. Mice were allocated into four groups of six mice each, as detailed in Table 5 below. Food was taken on the afternoon (18:00) of Day 0. Mice were orally administered APAP, APAP+NAC or APAP+NAC+IB 15 hours later (9:00 next morning, Day 1) by gavage administration. Food was returned 2 h after APAP administration (Day 1).

TABLE 5

Groups and treatment regimens

| Group | N | Treatment | Dosage (for treatment) | Admin. | fasting |
|---|---|---|---|---|---|
| A | 6 | APAP | 4 mg/mouse | PO | yes |
| B | 6 | APAP + NAC | APAP - 4 mg/mouse<br>NAC - 3.5 mg/mouse | PO | yes |
| C | 6 | APAP + NAC + IB | APAP - 4 mg/mouse<br>NAC - 3.5 mg/mouse<br>IB - 0.4 mg/mouse | PO | yes |
| D | 6 | APAP + NAC + IB | APAP - 4 mg/mouse<br>NAC - 3.5 mg/mouse<br>IB - 0.1 mg/mouse | PO | yes |

For all groups, mice were weighted daily, and blood samples were taken 24 h hours after APAP administration (Day 2) for liver enzyme tests. In addition, liver biopsies were performed. For histopathology, livers from individual mice were fixed in 10% formaldehyde solution and kept at room temperature until use. The tissue blocks were then embedded in paraffin, 5-mm sections were cut and stained with hematoxylin and eosin (H&E) for morphological examination. FIG. 1 shows representative histological liver sections from mice taken 24 h hours after APAP administration (×40 magnification). In the APAP group, diffuse damage to hepatocytes can be easily seen (hemorrhagic congestion and extensive centrilobular necrosis). Improved liver architecture with no evidence for cellular damage and necrosis can be seen in all treated groups.

Table 6 presents the effect of each combination on the serum levels of the liver enzymes ALT and AST.

TABLE 6

Serum levels of liver enzymes (IU/L)

| Group | ALT (average ± std. dev.) | AST (average ± std. dev.) |
|---|---|---|
| 4 mg APAP | 7,790.0 ± 2,175.9 | 4,883.3 ± 1,549.4 |
| 4 mg APAP + 3.5 mg NAC | 1,017.4 ± 752.1 | 1,905.5 ± 1,366.5 |
| 4 mg APAP + 3.5 mg NAC + 0.4 mg IB | 119.6 ± 61.9 | 400.9 ± 216.8 |
| 4 mg APAP + 3.5 mg NAC + 0.1 mg IB | 180.1 ± 36.0 | 335.1 ± 110.3 |

As can be seen from the above table, administration of APAP with a combination of 3.5 mg NAC+IB, either 0.1 or 0.4 mg, resulted in over 97% and 91% reduction in the serum levels of ALT and AST, respectively, compared to the administration of APAP only ($p<0.0001$). The combinations containing IB were significantly more effective than NAC alone ($p<0.05$).

In addition, mice that received APAP with NAC+IB showed a significantly higher increase in body weight between Day 1 and Day 2, compared to mice that received APAP only ($p<0.05$).

Example 4

Phosphatidylcholine (PC) in Combination with NAC

Mice were allocated into four groups of six mice each, as described in Table 7 below. Mice were treated according to the following procedure:

Food was taken on the afternoon (18:00) of Day 0. Mice were orally administered APAP, APAP+NAC or APAP+NAC+PC 15 h hours later (9:00 next morning, Day 1) by gavage administration as follows:

Group A: APAP
Group B: NAC+APAP
Group C: NAC+APAP, then 1.5 hours later: PC
Group D: NAC+APAP, then 3 hours later: PC For all groups, food was returned 3.5 h after APAP administration.

TABLE 7

Groups and treatment regimens

| Group | N | Treatment | Dosage (for treatment) | Admin. | fasting |
|---|---|---|---|---|---|
| A | 6 | APAP | 4 mg/mouse | PO | yes |
| B | 6 | APAP + NAC | APAP - 4 mg/mouse<br>NAC - 3 mg/mouse | PO | yes |
| C | 6 | APAP + NAC + PC | APAP - 4 mg/mouse<br>NAC - 3 mg/mouse<br>PC - 0.7 mg/mouse* | PO | yes |
| D | 6 | APAP + PC + NAC | APAP - 4 mg/mouse<br>NAC - 3 mg/mouse<br>PC - 0.7 mg/mouse** | PO | yes |

*PC was administered 1.5 hours after APAP + NAC administration
**PC was administered 3 hours after APAP + NAC administration For all groups, mice were weighted daily, and blood samples were taken 24 h hours after APAP administration (Day 2) for liver enzyme tests. In addition, liver biopsies were performed.

Figure 2:
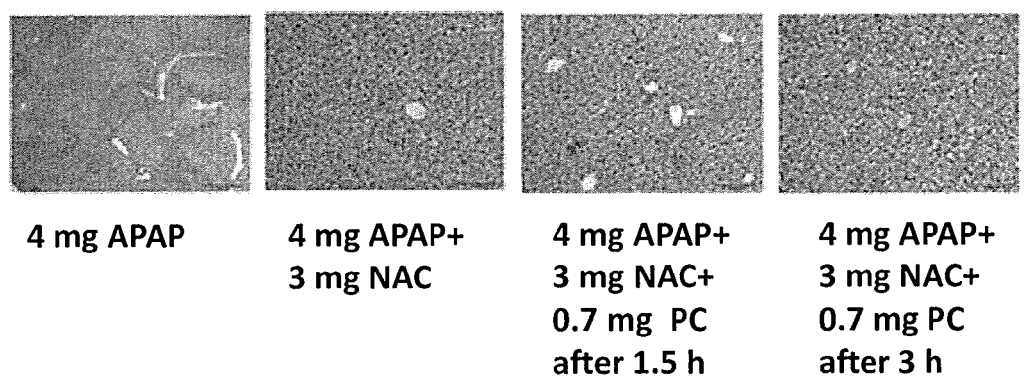
FIG. 2. Representative liver biopsy results of mice treated with acetaminophen in combination with NAC alone or NAC plus PC, compared to mice administered with acetaminophen only.

FIG. 2 shows representative histological liver sections from mice taken 24 h hours after APAP administration (×40 magnification). In APAP group, diffuse damage to hepatocytes can be easily seen (hemorrhagic congestion and extensive centrilobular necrosis). Improved liver architecture with no evidence for cellular damage and necrosis can be seen in all treated groups.

Table 8 presents the effect of each combination on the serum levels of the liver enzymes ALT and AST. Table 9 presents the effect of each combination on body weight loss, as determined by the ratio of the mice body weight between Day 0 and Day 2.

TABLE 8

Serum levels of liver enzymes (IU/L)

| Group | ALT (average ± std. dev.) | AST (average ± std. dev.) |
|---|---|---|
| 4 mg APAP | 6,421.67 ± 2,914.38 | 3,686.67 ± 2,168.08 |
| 4 mg APAP + 3 mg NAC | 240.50 ± 242.19 | 533.33 ± 454.07 |
| 4 mg APAP + 3 mg NAC + 0.7 mg PC after 1.5 h | 249.00 ± 230.15 | 519.33 ± 244.72 |
| 4 mg APAP + 3 mg NAC + 0.7 mg PC after 3 h | 193.50 ± 131.12 | 439.33 ± 195.63 |

As can be seen from the above table, administration of APAP with a combination of NAC+0.7 mg PC after 1.5 or 3 hrs resulted in about 96-97% and 86-88% reduction in the serum levels of ALT and AST, respectively, compared to the administration of APAP only ($p<0.01$).

TABLE 9

Effect on body weight

| Group | Weight ratio Day 0-Day 2 |
|---|---|
| 4 mg APAP | 94.17% |
| 4 mg APAP + 3 mg NAC | 96.70% |
| 4 mg APAP + 3 mg NAC + 0.7 mg PC after 1.5 h | 99.46% |
| 4 mg APAP + 3 mg NAC + 0.7 mg PC after 3 h | 99.15% |

As can be seen from the above table, mice that received APAP only showed a 6% decrease in their body weight during the two days of the experiment. The combination of NAC+PC (administered after 1.5 or 3 hours) almost completely prevented body weight loss, and was significantly more effective than NAC alone (~99% versus ~96%, p<0.00001).

Additional measurements have shown that administration of 0.8 mg/mouse PC 2-4 hours following APAP+NAC administration is also effective in reducing serum levels of ALT and AST and preventing body weight loss.

In another experiment testing NAC and PC, the following groups were evaluated:

TABLE 10

Groups and treatment regimens

| Group | N | Treatment | Dosage (for treatment) | Admin. | fasting |
|---|---|---|---|---|---|
| A | 6 | APAP | 4 mg/mouse | PO | yes |
| B | 6 | APAP + NAC | APAP - 4 mg/mouse<br>NAC - 3.5 mg/mouse | PO | yes |
| C | 6 | APAP + PC + NAC | APAP - 4 mg/mouse<br>NAC - 3.5 mg/mouse<br>PC - 0.9 mg/mouse* | PO | yes |

*PC was administered 3 hours after APAP + NAC administration

Figure 3:
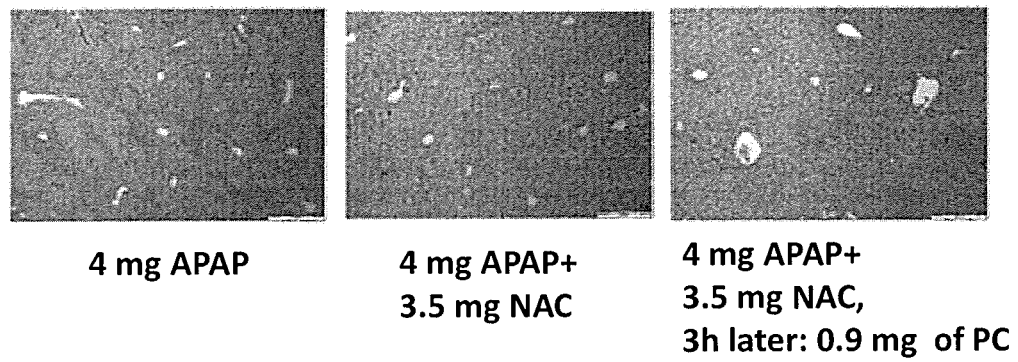
FIG. 3. Representative liver biopsy results of mice treated with acetaminophen in combination with NAC alone or NAC plus PC, compared to mice administered with acetaminophen only.

FIG. 3 shows representative histological liver sections from mice taken 24 h hours after APAP administration (×40 magnification). In APAP group, diffuse damage to hepatocytes can be easily seen (hemorrhagic congestion and extensive centrilobular necrosis). Improved liver architecture with no evidence for cellular damage and necrosis can be seen in all treated groups.

Table 11 presents the effect of each combination on the serum levels of the liver enzymes ALT and AST. Table 12 presents the effect of each combination on body weight loss, as determined by the ratio of the mice body weight between Day 0 and Day 2 and by the difference in the mice body weight between Day 1 (immediately after administration of APAP with the different combinations and before food was returned) and Day 2.

TABLE 11

Serum levels of liver enzymes (IU/L)

| Group | ALT (average ± std. dev.) | AST (average ± std. dev.) |
|---|---|---|
| 4 mg APAP | 7,530.00 ± 2,339.06 | 4,988.67 ± 878.44 |
| 4 mg APAP + 3.5 mg NAC | 242.95 ± 150.19 | 736.00 ± 257.63 |
| 4 mg APAP + 3.5 mg NAC 0.9 mg PC after 3 h | 232.50 ± 48.85 | 495.73 ± 148.52 |

As can be seen from the above table, administration of APAP with a combination of NAC+0.9 mg PC after 3 hrs resulted in about 97% and 89% reduction in the serum levels of ALT and AST, respectively, compared to the administration of APAP only (p<0.0001). The administration of NAC alone resulted in about 97% and 85% reduction in the serum levels of ALT and AST, respectively, compared to APAP only (p<0.0001).

TABLE 12

Effect on body weight

| Group | Weight ratio Day 1-Day 2 | Weight difference Day 1 - Day 2 |
|---|---|---|
| 4 mg APAP | 105% | 1.17 |
| 4 mg APAP + 3.5 mg NAC | 108% | 1.98 |
| 4 mg APAP + 3.5 mg NAC + 0.9 mg PC after 3 h | 109% | 2.38 |

As can be seen from the above table, mice that received APAP with NAC+PC 0.9 mg after 3 hours showed a significantly higher increase in body weight between Day 1 and Day 2, compared to mice that received APAP only (p<0.01). Administration of NAC alone did not show a significant effect.

In a further experiment testing NAC and PC, the following groups were evaluated:

TABLE 13

Groups and treatment regimens

| Group | N | Treatment | Dosage (for treatment) | Admin. | fasting |
|---|---|---|---|---|---|
| A | 6 | APAP | 4 mg/mouse | PO | yes |
| B | 6 | APAP | APAP - 4.6 mg/mouse | PO | yes |
| C | 6 | APAP + NAC + PC | APAP - 4 mg/mouse<br>NAC - 3.5 mg/mouse<br>PC - 0.9 mg/mouse* | PO | yes |
| D | 6 | APAP + PC + NAC | APAP - 4.6 mg/mouse<br>NAC - 3.5 mg/mouse<br>PC - 0.9 mg/mouse* | PO | yes |

*PC was administered 3 hours after APAP + NAC administration

Table 14 presents the effect of each combination on the serum levels of the liver enzymes ALT and AST. Table 15 presents the effect of each combination on body weight loss, as determined by the ratio of the mice body weight between Day 0 and Day 2 and by the difference in the mice body weight between Day 1 (immediately after administration of APAP with the different combinations and before food was returned) and Day 2.

TABLE 14

Serum levels of liver enzymes (IU/L)

| Group | ALT (average ± std. dev.) | AST (average ± std. dev.) |
|---|---|---|
| 4 mg APAP | 5,739.25 ± 2,536.44 | 4,374.00 ± 2,384.21 |
| 4.6 mg APAP | 7,772.50 ± 1,771.00 | 6,310.00 ± 2,127.07 |
| 4 mg APAP + 3.5 mg NAC 0.9 mg PC after 3 h | 937.00 ± 1,280.82 | 1,963.60 ± 2,563.99 |
| 4.6 mg APAP + 3.5 mg NAC 0.9 mg PC after 3 h | 230.00 ± 38.80 | 485.53 ± 168.47 |

TABLE 15

Effect on body weight

| Group | Weight ratio Day 1-Day 2 | Weight difference Day 1 – Day 2 |
|---|---|---|
| 4 mg APAP | 108% | 2.07 |
| 4.6 mg APAP | 104% | 1.02 |
| 4 mg APAP + 3.5 mg NAC 0.9 mg PC after 3 h | 110% | 2.70 |
| 4.6 mg APAP + 3.5 mg NAC 0.9 mg PC after 3 h | 110% | 2.55 |

As can be seen from the above tables, administration of APAP, either 4 or 4.6 mg, with a combination of f NAC+0.9 mg PC after 3 hrs resulted in a remarkable reduction in the serum levels of ALT and AST, and a significant higher increase in body weight between Day 1 and Day 2 compared to the administration of APAP only (p<0.01)

Example 5

Methylsulfonylmethane (MSM) in Combination with NAC

MSM in combination with NAC was tested for its effect on toxicity induced by APAP using the same procedure described in Example 1 above. Mice were allocated into three groups of six mice each, as detailed in Table 16 below. Food was taken on the afternoon (18:00) of Day 0. Mice were orally administered APAP, APAP+NAC or APAP+NAC+MSM 15 hours later (9:00 next morning, Day 1) by gavage administration. Food was returned 3.5 h after APAP administration (Day 1).

TABLE 16

Groups and treatment regimens

| Group | N | Treatment | Dosage (for treatment) | Admin. | fasting |
|---|---|---|---|---|---|
| A | 6 | APAP | 4 mg/mouse | PO | yes |
| B | 6 | APAP + NAC | APAP - 4 mg/mouse NAC - 3.5 mg/mouse | PO | yes |
| C | 6 | APAP + NAC + MSM | APAP - 4 mg/mouse NAC - 3.5 mg/mouse MSM - 1.5 mg/mouse | PO | yes |

Table 17 presents the effect of each combination on the serum levels of the liver enzymes ALT and AST. Table 18 presents the effect of each combination on body weight, as determined by the difference in the mice body weight between Day 1 (immediately after administration of APAP with the different combinations and before food was returned) and Day 2.

Figure 4:
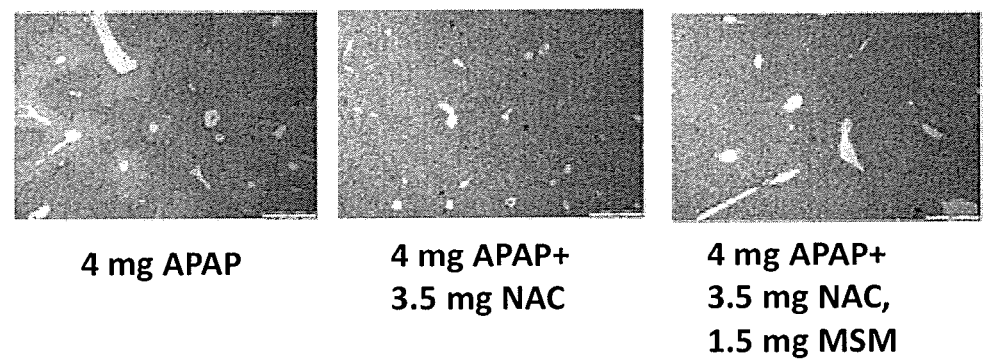
FIG. 4. Representative liver biopsy results of mice treated with acetaminophen in combination with NAC alone or NAC plus MSM, compared to mice administered with acetaminophen only.

FIG. 4 shows representative histological liver sections from mice taken 24 h hours after APAP administration (×40 magnification). In APAP group, diffuse damage to hepatocytes can be easily seen (hemorrhagic congestion and extensive centrilobular necrosis). Improved liver architecture with no evidence for cellular damage and necrosis can be seen in all treated groups.

TABLE 17

Serum levels of liver enzymes (IU/L)

| Group | ALT (average ± std. dev.) | AST (average ± std. dev.) |
|---|---|---|
| 4 mg APAP | 9,040 ± 3,472.64 | 6,560 ± 2,618.34 |
| 4 mg APAP + 3.5 mg NAC | 251.75 ± 112.65 | 1,215.73 ± 910.90 |
| 4 mg APAP + 3.5 mg NAC + 1.5 mg MSM | 194.88 ± 132.73 | 601.27 ± 325.63 |

As can be seen from the above table, administration of APAP with a combination of 3.5 mg NAC+1.5 mg MSM resulted in about 98% and 91% reduction in the serum levels of ALT and AST, respectively, compared to the administration of APAP only (p<0.001). The combination of NAC+MSM appeared to be more effective than NAC alone.

TABLE 18

Effect on body weight

| Group | Weight difference Day 1 – Day 2 |
|---|---|
| 4 mg APAP | 1.05 |
| 4 mg APAP + 3.5 mg NAC | 2.02 |
| 4 mg APAP + 3.5 mg NAC + 1.5 mg MSM | 2.12 |

As can be seen from the above table, mice that received APAP with 3.5 mg NAC+MSM 1.5 mg showed a significantly higher increase in body weight between Day 1 and Day 2, compared to mice that received APAP only (p<0.01). The combination of NAC+MSM appeared to be more effective than NAC alone.

Example 6

Combination of NAC, MSM, PC and IB

This combination was tested for its effect on toxicity induced by APAP using the procedure described in Example 1 above with several modifications, as described below. Mice were allocated into four groups of six mice each, as detailed in Table 19 below. Food was taken on the afternoon (18:00) of Day 0. Mice were orally administered APAP 15 hours later (9:00 next morning, Day 1) by gavage administration. NAC was administered PO with APAP. MSM+IB were administered 1.5 h later. Following another 1.5 h, PC was administered. Food was returned 3.5 h after APAP administration (Day 1). Weight was determined three times: on Day 0 before food was taken, after over-night fasting (Day 1, just before APAP administration) and before sacrifice (Day 2, 24 hours after APAP administration).

TABLE 19

Groups and treatment regimens

| Group | N | Treatment | Dosage (for treatment) | Admin. | fasting |
|---|---|---|---|---|---|
| A | 6 | APAP | 7 mg/mouse | PO | yes |
| B | 6 | APAP + NAC | APAP - 7 mg/mouse NAC - 3.5 mg/mouse | PO | yes |
| C | 6 | APAP + NAC + MSM + PC + IB | APAP - 7 mg/mouse 3.5 mg/mouse NAC 0.1 mg/mouse MSM 0.1 mg/mouse IB 0.9 mg/mouse PC | PO | yes |
| D | 6 | APAP + NAC + MSM + PC + IB | APAP - 7 mg/mouse 3.5 mg/mouse NAC 0.2 mg/mouse MSM 0.1 mg/mouse IB 0.9 mg/mouse PC | PO | yes |

Table 20 presents the effect of each combination on the serum levels of the liver enzymes ALT and AST. Table 21 presents the effect of each combination on body weight, as determined by the difference/ratio in the mice body weight between Day 1 and 2.

TABLE 20

Serum levels of liver enzymes (IU/L)

| Group | ALT (average ± std. dev.) | AST (average ± std. dev.) |
|---|---|---|
| 7 mg APAP | 20,160.00 ± 9,678.28 | 20,001.00 ± 11,998.16 |
| 7 mg APAP + 3.5 mg NAC | 6,320.40 ± 4,659.56 | 5,252.40 ± 4,532.30 |
| 7 mg APAP + 3.5 mg NAC + 1.5 h - 0.1 mg IB + 0.1 mg MSM + 3 h- 0.9 mg PC | 3,803.15 ± 3,453.52 | 2,331.13 ± 1,808.88 |
| 7 mg APAP + 3.5 mg NAC + 1.5 h - 0.1 mg IB + 0.2 mg MSM + 3 h- 0.9 mg PC | 4,124.50 ± 2,824.25 | 2,274.67 ± 1,171.34 |

TABLE 21

Effect on body weight

| Group | Weight ratio Day 1-Day 2 | Weight difference Day 1 – Day 2 |
|---|---|---|
| 7 mg APAP | 98% | −0.45 |
| 7 mg APAP + 3.5 mg NAC | 100% | 0.08 |
| 7 mg APAP + 3.5 mg NAC + 1.5 h - 0.1 mg IB + 0.1 mg MSM + 3 h- 0.9 mg PC | 103% | 0.87 |
| 7 mg APAP + 3.5 mg NAC + 1.5 h - 0.1 mg IB + 0.2 mg MSM + 3 h- 0.9 mg PC | 104% | 0.98 |

As can be seen from the above tables, administration of 7 mg APAP per mouse resulted in severe intoxication. Administration of NAC in combination with IB, MSM and PC resulted in a major reduction of the serum levels of ALT and AST, and a significantly higher increase in body weight between Day 1 and Day 2 compared to the administration of APAP only. This combination was more effective than NAC alone.

Example 7

Combination of MSM and IB

This combination was tested for its effect on toxicity induced by APAP using the procedure described in Example 1 above.

TABLE 22

Groups and treatment regimens

| Group | N | Treatment | Dosage (for treatment) | Admin. | fasting |
|---|---|---|---|---|---|
| A | 6 | APAP | 4 mg/mouse | PO | yes |
| B | 6 | APAP + MSM | APAP - 4 mg/mouse MSM - 0.15 mg/mouse | PO | yes |
| C | 6 | APAP + IB | APAP - 4 mg/mouse 0.1 mg/mouse IB | PO | yes |
| D | 6 | APAP + MSM + IB | APAP - 4 mg/mouse MSM - 0.15 mg/mouse 0.1 mg/mouse IB | PO | yes |

TABLE 23

Serum levels of liver enzymes (IU/L)

| Group | ALT (average ± std. dev.) | AST (average ± std. dev.) |
|---|---|---|
| 4 mg APAP | 8,918.00 ± 2,955.74 | 6,586.67 ± 4,204.58 |
| 4 mg APAP + 0.15 mg MSM | 5,775.62 ± 3,124.91 | 3,759.07 ± 2,638.37 |
| 4 mg APAP + 0.1 mg IB | 6,414.40 ± 5,175.92 | 3,785.60 ± 3,014.24 |
| 4 mg APAP + 0.15 mg MSM 0.1 mg IB | 1,712.40 ± 2,857.95 | 908.60 ± 1,092.20 |

As can be seen from the above table, a combination of MSM and IB showed significant reduction of the serum levels of ALT and AST ($p<0.05$). The combination was superior to each of the compounds alone, which did not show a significant effect.

In another experiment testing MSM and IB, the following groups were evaluated:

TABLE 24

Groups and treatment regimens

| Group | N | Treatment | Dosage (for treatment) | Admin. | fasting |
|---|---|---|---|---|---|
| A | 6 | APAP | 4 mg/mouse | PO | yes |
| B | 6 | APAP + MSM | APAP - 4 mg/mouse MSM - 0.25 mg/mouse | PO | yes |
| C | 6 | APAP + IB | APAP - 4 mg/mouse 0.1 mg/mouse IB | PO | yes |
| D | 6 | APAP + MSM + IB | APAP - 4 mg/mouse MSM - 0.25 mg/mouse 0.1 mg/mouse IB | PO | yes |

TABLE 25

Serum levels of liver enzymes (IU/L)

| Group | ALT (average ± std. dev.) | AST (average ± std. dev.) |
|---|---|---|
| 4 mg APAP | 6,896.00 ± 2,998.94 | 4,303.33 ± 2,163.30 |
| 4 mg APAP + 0.25 mg MSM | 8,502.00 ± 2,186.33 | 5,076.00 ± 1,616.62 |
| 4 mg APAP + 0.1 mg IB | 6,882.00 ± 3,191.25 | 4,156.67 ± 2,136.22 |
| 4 mg APAP + 0.25 mg MSM 0.1 mg IB | 3,066.20 ± 2,802.32 | 1,830.67 ± 1,570.80 |

Once again, the combination of MSM and IB in group D showed significant reduction of the serum levels of ALT and AST (p<0.05). The combination was much superior to each of the compounds alone, which did not show any meaningful effect.

In order to determine that the combination of MSM+IB does not interfere with the anti-inflammatory effect of APAP, splenocytes were isolated from mice from each group and tested for their IFN-γ secretion. After mice were sacrificed, spleens from five mice from each group were taken and splenocytes were isolated by the following procedure:

Isolation of splenocytes: Spleens were stored in RPMI-1640 medium supplemented with FCS. Spleens were crushed through a 70-μm nylon cell strainer (Falcon) and centrifuged (1,250 rpm for 7 min.). Red blood cells were lysed in 1 ml of cold 155 mM ammonium chloride lysis buffer. Splenocytes were washed and resuspended in 1 ml of RPMI supplemented with FCS. The viability of cells as assessed by trypan blue exclusion exceeded 90%.

Next, splenocytes ($1 \times 10^6$ per mouse, per well, in duplicates) were moved into a 24 well plate containing RPMI-1640 supplemented with 10% FCS, 1% penicillin/streptomycin (P/S), 1% glutamine, 1% sodium pyruvate and 1% non-essential amino acid. All splenocytes were activated with 5 μg of Concanavalin A (purchased from MP Biomedicals, Ohio, USA), for 20 h at 37° C. After incubation cells from all wells were moved to Eppendorff tubes and centrifuged for 5 minutes. Then supernatants were collected and freezed in –80° C. until assayed for IFN-γ by ELISA.

Cytokine determination: Levels of IFN-γ were determined by "sandwich" ELISA using commercial kit according to the manufacturer's instructions (Quantikine, R&D Systems, Minneapolis, Minn., USA).

Figure 5:
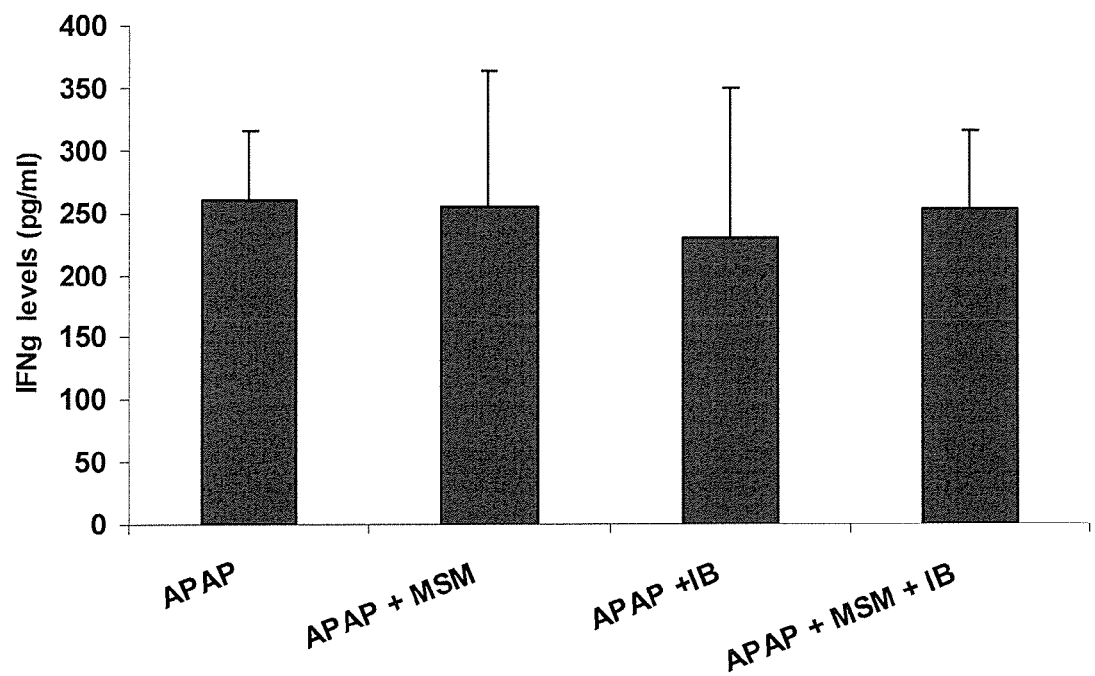
FIG. 5. IFN-γ levels secreted by ConA-activated splenocytes derived from acetaminophen-intoxicated mice.

FIG. 5 shows IFN-γ levels secreted by ConA-activated splenocytes derived from each group of mice. As can be seen in the figure, the combination of MSM+IB had no effect on the secretion of IFN-γ from in vitro ConA-activated splenocytes (259, 255, 229, 253 pg/ml of IFN-γ, for groups A, B, C and D, respectively, p=NS).

Thus, the results have shown that oral administration of the above combination of MSM+IB with APAP is associated with a similar anti-inflammatory effect to that of APAP, while significantly alleviating the APAP-induced liver injury.

In another experiment the effect of the IB+MSM combination on APAP absorption was tested. Mice treated with 10 mg of APAP alone or in combination with 0.1 mg IB+0.25 mg MSM were followed for APAP serum levels. The results have shown that the combination of IB+MSM had no effect on the bioavailability of APAP. Serum levels of APAP in mice treated with 10 mg of APAP alone were similar to mice treated with APAP+IB+MSM (129 vs. 149 μg/ml, respectively. p=NS).

Example 8

Combinations with Cys and Met

Mice were allocated into four groups of six mice each, as described in Table 26 below. The mice received sub-lethal hepatotoxic doses of APAP (4.6 mg/mouse). The effect of the different combinations of compounds on toxicity induced by APAP was tested using the procedure described in Example 1 above.

TABLE 26

Groups and treatment regimens

| Group | N | Treatment | Dosage (for treatment) | Admin. | fasting |
|---|---|---|---|---|---|
| A | 6 | APAP | 4.6 mg/mouse | PO | yes |
| B | 6 | APAP + NAC | APAP - 4 mg/mouse<br>NAC - 3.5 mg/mouse | PO | yes |
| C | 6 | APAP + Cys + PC + MSM + IB | APAP - 4.6 mg/mouse<br>Cys - 3.5 mg/mouse<br>PC - 0.9 mg/mouse<br>MSM- 0.2 mg/mouse<br>IsoB- 0.1 mg/mouse | PO | yes |
| D | 6 | APAP + Met + PC + MSM + IB | APAP - 4.6 mg/mouse<br>Met - 3.5 mg/mouse<br>PC - 0.9 mg/mouse<br>MSM- 0.2 mg/mouse<br>IsoB- 0.1 mg/mouse | PO | yes |

Figure 6:
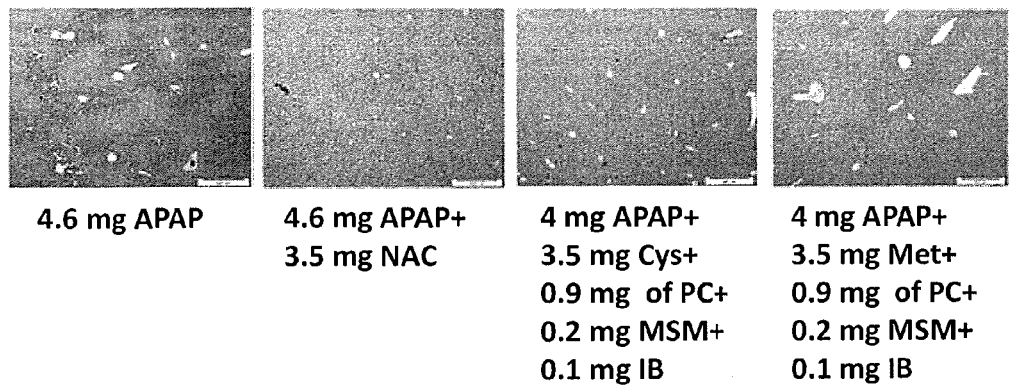
FIG. 6. Representative liver biopsy results of mice treated with acetaminophen, acetaminophen plus NAC, acetaminophen plus Cys, PC, MSM and IB, or acetaminophen plus Met, PC, MSM and IB.

FIG. 6 shows representative histological liver sections from mice taken 24 h hours after APAP administration (×40 magnification). In APAP group, diffuse damage to hepatocytes can be easily seen (hemorrhagic congestion and extensive centrilobular necrosis). Improved liver architecture with no evidence for cellular damage and necrosis can be seen in all treated groups.

Table 27 presents the effect of each combination on the serum levels of the liver enzymes ALT and AST. Table 28 presents the effect of each combination on body weight loss, as determined by the ratio of the mice body weight between Day 0 and Day 2.

TABLE 27

Serum levels of liver enzymes (IU/L)

| Group | ALT (average ± std. dev.) | AST (average ± std. dev.) |
|---|---|---|
| 4.6 mg APAP | 10285.00 ± 4435.22 | 7796.00 ± 5000.46 |
| 4.6 mg APAP + 3.5 mg NAC | 351.00 ± 234.54 | 348.80 ± 60.96 |
| 4.6 mg APAP + 3.5 mg Cys + 0.9 mg PC + 0.2 mg MSM + 0.1 mg IB | 297.15 ± 228.61 | 445.20 ± 164.51 |
| 4.6 mg APAP + 3.5 mg Met + 0.9 mg PC + 0.2 mg MSM + 0.1 mg IB | 476.58 ± 670.28 | 417.20 ± 148.61 |

As can be seen from the above table, administration of APAP in combination of NAC resulted in about 95-97% reduction in the serum levels of ALT and AST, compared to the administration of APAP only (p<0.005). Similarly, administration of APAP and NAC substitutes (Cys or Met) in combination with PC, MSM and IB resulted in a comparable decrease in liver enzymes.

TABLE 28

Effect on body weight

| Group | Weight ratio Day 0-Day 2 |
|---|---|
| 4.6 mg APAP | 91.59% |
| 4.6 mg APAP + 3.5 mg NAC | 101.60% |
| 4.6 mg APAP + 3.5 mg Cys + 0.9 mg PC + 0.2 mg MSM + 0.1 mg IB | 99.21% |
| 4.6 mg APAP + 3.5 mg Met + 0.9 mg PC + 0.2 mg MSM + 0.1 mg IB | 99.10% |

As can be seen from the above table, mice that received APAP only showed more than 8% decrease in their body weight during the two days of the experiment. The combination of NAC substitutes with PC, MSM and IB almost completely prevented body weight loss, and was more effective as NAC alone (p<0.01).

In another experiment the following groups were evaluated:

TABLE 29

Groups and treatment regimens

| Group | N | Treatment | Dosage (for treatment) | Admin. | fasting |
|---|---|---|---|---|---|
| A | 6 | APAP | 4.6 mg/mouse | PO | yes |
| B | 6 | APAP + NAC + PC + MSM + IB | APAP - 4.6 mg/mouse NAC - 3.5 mg/mouse PC - 0.9 mg/mouse** MSM - 0.1 mg/mouse* IsoB - 0.1 mg/mouse* | PO | yes |
| C | 6 | APAP + Cys + PC + MSM + IB | APAP - 4.6 mg/mouse Cys - 3.5 mg/mouse PC - 0.9 mg/mouse** MSM - 0.1 mg/mouse* IsoB - 0.1 mg/mouse* | PO | yes |
| D | 6 | APAP + Met + PC + MSM + IB | APAP - 4.6 mg/mouse Met - 3.5 mg/mouse PC - 0.9 mg/mouse** MSM - 0.1 mg/mouse* IB - 0.1 mg/mouse* | PO | yes |

*MSM and IB were administered 1.5 hours after APAP + NAC or after APAP + Cys or after APAP + Met, were administered.
**PC was administered 3 hours after APAP + NAC or after APAP + Cys or after APAP + Met; were administered.

Figure 7:
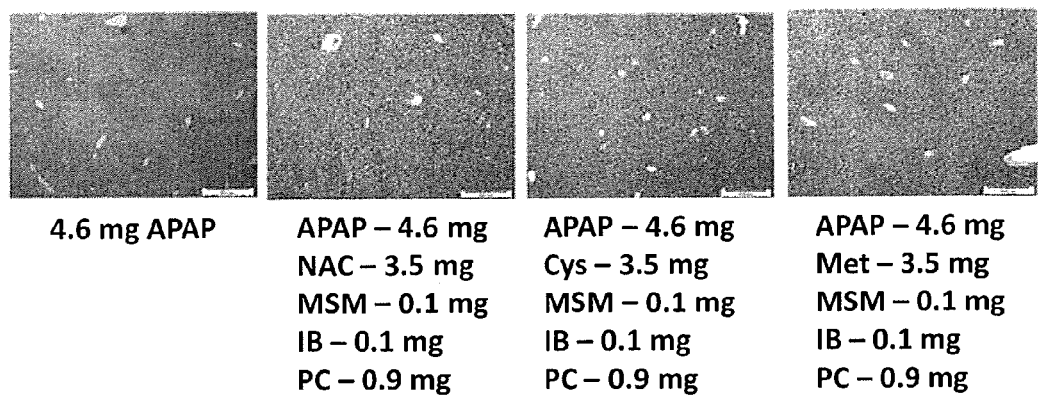
FIG. 7. Representative liver biopsy results of mice treated with acetaminophen, acetaminophen plus NAC, PC, MSM and IB, acetaminophen plus Cys, PC, MSM and IB, or acetaminophen plus Met, PC, MSM and IB.

Mice were treated according to the following procedure:
Food was taken on the afternoon (18:00) of Day 0. Mice were orally administered various preparations (as mentioned in Table 31) 15 h hours later (9:00 next morning, Day 1) by gavage administration as follows:

Group A: APAP
Group B: NAC+APAP. After 1.5 h, MSM+IB. After another 1.5 h, PC
Group C: APAP+Cys. After 1.5 h, MSM+IB. After another 1.5 h, PC
Group D: APAP+Met. After 1.5 h, MSM+IB). After another 1.5 h, PC FIG. 7 shows representative histological liver sections from mice taken 24 h hours after APAP administration (×40 magnification). In APAP group, diffuse damage to hepatocytes can be easily seen (hemorrhagic congestion and extensive centrilobular necrosis). Improved liver architecture with no evidence for cellular damage and necrosis can be seen in all treated groups.

Table 30 presents the effect of each combination on the serum levels of the liver enzymes ALT and AST. Table 31 presents the effect of each combination on body weight loss, as determined by the ratio of the mice body weight between Day 0 and Day 2.

TABLE 30

Serum levels of liver enzymes (IU/L)

| Group | ALT (average_ ± std. dev.) | AST (average_ ± std. dev.) |
|---|---|---|
| APAP | 11210.83 ± 7589.19 | 10577.33 ± 11375.63 |
| APAP + NAC + PC + MSM + IB | 545.98 ± 576.09 | 460.27 ± 205.92 |
| APAP + Cys + PC + MSM + IB | 126.18 ± 84.75 | 258.57 ± 71.45 |
| APAP + Met + PC + MSM + IB | 178.90 ± 34.79 | 278.83 ± 108.56 |

As can be seen from the above table, administration of APAP with a combination of NAC with later on administration of MSM, IB and afterwards PC, resulted in about 95-96% reduction in the serum levels of ALT and AST, compared to the administration of APAP only (p<0.07). When NAC was replaced by either Cys or Met, the effect on liver enzymes even increased to 98-99% reduction in ALT levels and 97-98% reduction in AST levels compared to the administration of APAP only (p<0.005).

TABLE 31

Effect on body weight

| Group | Weight ratio Day 0-Day 2 |
|---|---|
| APAP | 91.23% |
| APAP + NAC + PC + MSM + IB | 96.13% |
| APAP + Cys + PC + MSM + IB | 97.02% |
| APAP + Met + PC + MSM + IB | 98.35% |

As can be seen from the above table, mice that received APAP only showed more than 8% decrease in their body weight during the two days of the experiment. The combination of NAC with PC, MSM and IB lowered body weight loss to 96.13%. When NAC was replaced by either Cys or Met, the effect on body weight was similar and even slightly increased to 97-98% (p<0.007).

In another experiment the following groups were evaluated:

TABLE 32

Groups and treatment regimens

| Group | N | Treatment | Dosage (for treatment) | Admin. | fasting |
|---|---|---|---|---|---|
| A | 6 | APAP | 4.6 mg/mouse | PO | yes |
| B | 6 | APAP + NAC+ | APAP - 4.6 mg/mouse NAC- 3.5 mg/mouse | PO | yes |
| C | 6 | APAP + Cys | APAP - 4.6 mg/mouse Cys - 3.5 mg/mouse | PO | yes |
| D | 6 | APAP + Met | APAP - 4.6 mg/mouse Met - 3.5 mg/mouse | PO | yes |

Mice were treated according to the procedure describe in Example 1 above.

Figure 8:
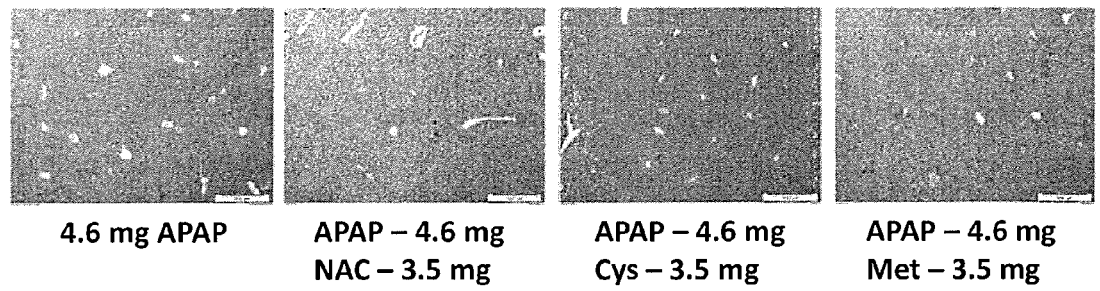
FIG. 8. Representative liver biopsy results of mice treated with acetaminophen, acetaminophen plus NAC, acetaminophen plus Cys, or acetaminophen plus Met.

FIG. 8 shows representative histological liver sections from mice taken 24 h hours after APAP administration (×40 magnification). In APAP group, diffuse damage to hepatocytes can be easily seen (hemorrhagic congestion and extensive centrilobular necrosis). Improved liver architecture with no evidence for cellular damage and necrosis can be seen in all treated groups.

Table 33 presents the effect of various treatments on the serum levels of the liver enzymes ALT and AST. Table 34 presents the effect of each combination on body weight loss, as determined by the ratio of the mice body weight between Day 0 and Day 2.

TABLE 33

Serum levels of liver enzymes (IU/L)

| Group | ALT (average_ ± std. dev.) | AST (average_ ± std. dev.) |
|---|---|---|
| APAP | 9002.50 ± 4211.03 | 5684.00 ± 2307.64 |
| APAP + NAC | 1175.26 ± 1552.79 | 821.93 ± 766.57 |
| APAP + Cys | 196.06 ± 112.80 | 369.47 ± 117.51 |
| APAP + Met | 147.84 ± 49.24 | 332.97 ± 100.52 |

As can be seen from the above table, administration of APAP with NAC resulted in about 85-87% reduction in the serum levels of ALT and AST compared to administration of APAP alone. Administration of APAP with Cys or Met resulted in a greater reduction in the liver enzymes, up to about 94-98% reduction compared to APAP alone ($p<0.0005$).

TABLE 34

Effect on body weight

| Group | Weight ratio Day 0-Day 2 |
|---|---|
| APAP | 93.26% |
| APAP + NAC | 98.08% |
| APAP + Cys | 97.89% |
| APAP + Met | 99.45% |

As can be seen from the above table, mice that received APAP only showed more than 6% decrease in their body weight during the two days of the experiment. The combination of APAP with NAC resulted in lower weight loss, to 98.08%. When NAC was replaced by either Cys or Met, the effect on body weight was similar (97-99% $p<0.007$).

The foregoing description of the specific embodiments will so fully reveal the general nature of the invention that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The invention claimed is:

1. A pharmaceutical composition comprising acetaminophen in combination with isolated isosilybin B, wherein the isolated isosilybin B is at least 80% separated from other milk thistle extract components, and optionally further comprising at least one additional protective agent selected from the group consisting of methylsulfonylmethane (MSM), phosphatidylcholine, cysteine (Cys), seleno-cysteine (Se-Cys), ribose-cysteine (RibCys), N-acetylcysteine (NAC), N-acetylcysteine-amide (AD4), methionine (Met) and S-adenosylmethionine (SAM).

2. The pharmaceutical composition of claim 1, further comprising (i) one or more protective agents selected from the group consisting of Cys, Se-Cys, RibCys, NAC, AD4, Met and SAM; and (ii) one or more protective agents selected from the group consisting of MSM and phosphatidylcholine.

3. The pharmaceutical composition of claim 1, further comprising at least one additional drug selected from the group consisting of an opioid analgesic, a decongestant, a cough suppressant, an antihistamine and an expectorant.

4. The pharmaceutical composition of claim 1, wherein the pharmaceutical composition is formulated for a route of administration selected from the group consisting of oral, rectal, intravenous, intramuscular, intradermal, subcutaneous and intranasal.

5. The pharmaceutical composition of claim 1, wherein said isolated isosilybin B is at least 90% separated from other milk thistle extract components.

6. The pharmaceutical composition of claim 1, wherein said isolated isosilybin B is isosilybin B purified from an extract of *Silybum marianum*.

7. The pharmaceutical composition of claim 1, wherein said isolated isosilybin B is a synthetic isosilybin B.

8. The pharmaceutical composition of claim 1, further comprising one or more protective agents selected from the group consisting of Cys, Se-Cys, RibCys, NAC, AD4, Met and SAM.

* * * * *